US012609200B2

(12) United States Patent
Kim

(10) Patent No.: US 12,609,200 B2
(45) Date of Patent: Apr. 21, 2026

(54) NEURAL PROCESSING UNIT FOR CARDIOVASCULAR DISEASE PREDICTION ARTIFICIAL NEURAL NETWORK MODEL

(71) Applicant: DEEPX CO., LTD., Seongnam-si (KR)

(72) Inventor: Lokwon Kim, Seongnam-si (KR)

(73) Assignee: DEEPX CO., LTD., Seongnam-si (KR)

( * ) Notice: Subject to any disclaimer, the term of this patent is extended or adjusted under 35 U.S.C. 154(b) by 274 days.

(21) Appl. No.: 18/134,544

(22) Filed: Apr. 13, 2023

(65) Prior Publication Data

US 2024/0145086 A1      May 2, 2024

(30) Foreign Application Priority Data

Oct. 31, 2022    (KR) ........................ 10-2022-0142481

(51) Int. Cl.
  *G16H 50/20*      (2018.01)
  *G06N 3/063*      (2023.01)
  *G16H 50/30*      (2018.01)
(52) U.S. Cl.
  CPC ............. *G16H 50/20* (2018.01); *G06N 3/063* (2013.01)
(58) Field of Classification Search
  CPC ................................ G16H 50/20; G06N 3/063
  See application file for complete search history.

(56) References Cited

U.S. PATENT DOCUMENTS

2017/0103305 A1* 4/2017 Henry ..................... G06N 3/044
2021/0232208 A1* 7/2021 Schirmer ................. G06N 3/04

FOREIGN PATENT DOCUMENTS

| KR | 10-2020-0068161 A | 6/2020 | |
|----|----|----|----|
| KR | 10-2020-0139343 A | 12/2020 | |
| KR | 10-2022-0078819 A | 6/2022 | |
| KR | 10-2022-0081277 A | 6/2022 | |
| KR | 10-2022-0097161 A | 7/2022 | |
| WO | WO-2018219809 A1 * | 12/2018 | ........... A61B 5/0002 |
| WO | WO-2020047171 A1 * | 3/2020 | ........... A61B 5/0022 |
| WO | WO-2022050578 A1 * | 3/2022 | ........... G06K 9/6267 |
| WO | WO-2022198050 A1 * | 9/2022 | ............... G06T 7/11 |

OTHER PUBLICATIONS

Chen et al., ECG Signal-Enabled Automatic Diagnosis Technology of Heart Failure, Nov. 3, 2021, J Healthc Eng (Year: 2021).*

* cited by examiner

*Primary Examiner* — Marc Q Jimenez
*Assistant Examiner* — Alexis K. Van Duzer
(74) *Attorney, Agent, or Firm* — INVENSTONE PATENT, LLC

(57) ABSTRACT

A neural processing unit includes a controller to receive a compiled machine code of an artificial neural network (ANN) model for predicting cardiovascular disease, the ANN model configured to receive sensing data of ECG, respiration, pulse rate, acceleration, and/or body temperature and to output a probability of disease onset for cerebral infarction, heart failure, and/or ischemic heart disease in a user; an input circuit configured to receive a plurality of input signals corresponding to the ANN model; a processing element (PE) array to perform a calculation of the ANN model; a special function unit (SFU) to perform a special function of calculating the ANN model; and an on-chip memory to store operation data of the ANN model, wherein the controller controls the PE array, the SFU, and the on-chip memory to process the ANN model according to data locality information of the ANN model included in the compiled machine code.

19 Claims, 27 Drawing Sheets

110-10

Convolution    Pooling    Convolution    Pooling    Fully Connected    Fully Connected    Output Predictions Feature Map Channels

| LAYER | MEMORY MAP | | OPERATION MODE | Data type | ANN DATA LOCALITY | DATA SIZE (Byte) |
|---|---|---|---|---|---|---|
| | Start address | end address | | | | |
| 1 | 0 | A=A' | Read | IFMAP | 1 | A |
| 1 | A'+1 | A+1+B=B' | Read | Kernel | 2 | B |
| 1 | B'+1 | B'+1+C=C' | Write | OFMAP | 3 | C |
| 2 | B'+1 | B'+1+C=C' | Read | IFMAP | 4 | C |
| 2 | C'+1 | C'+1+D=D' | Read | Kernel | 5 | D |
| 2 | D'+1 | D'+1+E=E' | Write | OFMAP | 6 | E |
| 3 | D'+1 | D'+1+E=E' | Read | IFMAP | 7 | E |
| 3 | E'+1 | E'+1+F=F' | Read | Kernel | 8 | F |
| 3 | F'+1 | F'+1+G=G' | Write | OFMAP | 9 | G |
| 4 | F'+1 | F'+1+G=G' | Read | IFMAP | 10 | G |
| 4 | G'+1 | G'+1+H=H' | Read | Kernel | 11 | H |
| 4 | H'+1 | H'+1+I=I' | Write | OFMAP | 12 | I |
| 1 | B'+1 | B'+1+C=C' | Read | SKIP CONNECTION | 13 | C |
| 5 | H'+1 | H'+1+I=I' | Read | Kernel | 14 | I |
| 5 | I'+1 | I'+1+J=J' | Read | OFMAP | 15 | J |
| 5 | J'+1 | J'+1+K=K' | Write | IFMAP | 16 | K |

NEURAL PROCESSING UNIT FOR CARDIOVASCULAR DISEASE PREDICTION ARTIFICIAL NEURAL NETWORK MODEL

BACKGROUND OF THE DISCLOSURE

Technical Field

The present disclosure relates to a neural processing unit for an artificial neural network model for predicting cardio-vascular disease.

Background Art

With the entry into an aging society, the population suffering from cardiovascular disease (CDV) due to aging and consequent physical and cognitive impairments is increasing. Recently, various studies have been conducted to recognize this phenomenon as a social problem and to diagnose and treat the disease in advance.

For example, sensing data related to a user may be continuously acquired using a wearable device. In addition, there has been disclosed a technique of monitoring the disease to secure diagnostic data related to the disease and self-diagnosing disease in the user.

However, disease in a user is still diagnosed based only on the results that can be confirmed fragmentarily from the sensing data. Accordingly, there are problems in that the accuracy of disease diagnosis is low and the number of diseases that can be diagnosed is limited. In addition, in a device possessed by a user, various and large amounts of sensing data acquired through the user are processed in real time. Therefore, there is a problem of consuming a lot of processing time and power to obtain the result (e.g., disease occurrence probability).

In order to accurately diagnose a user's disease, it is still necessary to send individual sensing data to a server capable of diagnosing the disease. In this case, there is a risk of leakage of personal information.

The background technology of this disclosure was described to facilitate understanding of this disclosure. It should not be construed as an admission that matters described in the background of this disclosure exist as prior art.

SUMMARY OF THE DISCLOSURE

Accordingly, there is needed a neural processing unit (NPU) for accurately diagnosing a disease based on various sensing data obtained from a device owned by a user.

As a result, the inventors of the present disclosure attempted to develop a neural processing unit capable of implementing an artificial neural network model for diagnosing and predicting a user's disease by combining different sensing data associated with the user.

In particular, the inventors of the present disclosure have developed a neural processing unit capable of more quickly and accurately processing cardiovascular diseases by performing a concatenation operation and a skip-connection operation capable of effectively processing different data.

The tasks of the present disclosure are not limited to the tasks mentioned above, and other tasks not mentioned will be clearly understood by those skilled in the art from the following description.

According to an example of the present disclosure, there is provided a neural processing unit (NPU). The NPU may include a controller configured to receive a compiled machine code of an artificial neural network (ANN) model for predicting cardiovascular disease, the ANN model configured to receive sensing data of at least one of ECG, respiration, pulse rate, acceleration, and body temperature and to output a probability of disease onset for at least one disease among cerebral infarction, heart failure, and ischemic heart disease; an input circuit configured to receive a plurality of input signals corresponding to the ANN model; a processing element (PE) array configured to perform a calculation of the ANN model; a special function unit (SFU) configured to perform a special function of calculating the ANN model; and an on-chip memory configured to store operation data of the ANN model. The controller may be further configured to control the PE array, the SFU circuit, and the on-chip memory to process the ANN model in a predetermined order according to data locality information of the ANN model included in the compiled machine code.

The ANN model may be further configured to output the probability of disease onset for the at least one disease by inputting the sensing data of at least two of the ECG, the respiration, the pulse rate, the acceleration, and the body temperature.

The ANN model may be further configured to input the sensing data of at least two of the ECG, the respiration, the pulse rate, the acceleration, and the body temperature and to output a probability of disease onset for at least two diseases among cerebral infarction, heart failure, and ischemic heart disease.

The NPU may further include an output unit configured to output a diagnosis result of the at least one disease of the ANN model, and the ANN model may be trained to process an inference operation of at least one of classification, semantic segmentation, object detection, and prediction by the PE array.

The SFU may have at least one function of a skip-connection and a concatenation for fusion of artificial neural networks.

The controller may include a schedular, and the scheduler may be configured to control the on-chip memory to preserve specific data stored in the on-chip memory up to a specific operation stage of the ANN model based on data locality information of the ANN model.

The PE array may include a plurality of threads, and the controller may be further configured to control the plurality of threads to process a parallel section of the ANN model based on data locality information of the ANN model.

According to another example of the present disclosure, there is provided a neural processing unit (NPU). The NPU may include a controller configured to receive a machine code of an artificial neural network (ANN) model for predicting cardiovascular disease, the ANN configured to input sensing data of at least one of ECG, respiration, pulse rate, acceleration, and body temperature and to output a probability of disease onset for at least one disease among cerebral infarction, heart failure, and ischemic heart disease; a processing element (PE) array configured to perform computation of the ANN model based on the machine code; and a special function unit (SFU) configured to compute a corresponding special function by receiving a convolution operation value processed by the PE array. The SFU may include a plurality of function units and may be further configured to selectively control at least one of the plurality of function units according to data locality information of the ANN model included in the machine code.

The plurality of function units may be configured in a pipeline structure.

The plurality of function units may be configured to be selectively activated by the controller or to be selectively deactivated by the controller.

Each of the plurality of function units may configured to be selectively clock-gated for each specific operation stage by the controller or to be selectively power-gated for each specific operation stage by the controller.

The NPU may further include an input unit configured to receive a plurality of input signals corresponding to the ANN model; and an on-chip memory configured to store computation data of the ANN model.

The NPU may further include a batch input unit configured to receive a plurality of input signals corresponding to the ANN model in a batch-mode; an on-chip memory configured to store computation data of the ANN model in the batch-mode; and an output unit configured to output at least one inference result of the ANN model. The ANN model may be trained to process an inference operation of at least one of classification, semantic segmentation, object detection, and prediction by the PE array in the batch-mode.

According to another example of the present disclosure, there is provided a system. The system may include at least one neural processing unit including a controller configured to receive a machine code of an artificial neural network (ANN) model for predicting cardiovascular disease, the ANN model configured to input sensing data of at least one of ECG, respiration, pulse rate, acceleration, and body temperature and to output a probability of disease onset for at least one disease among cerebral infarction, heart failure, and ischemic heart disease, an input unit configured to receive at least one input signal, a processing element array configured to perform a convolution operation, and an on-chip memory configured to store a result of the convolution operation; and a memory controller including a memory, the memory controller configured to receive data locality information of the ANN model and to cache a next memory operation request to be requested by a corresponding one of the at least one neural processing unit based on the data locality information, the data locality information of the ANN model being capable of predicting successive memory operation requests of the at least one neural processing unit.

The at least one neural processing unit may be plural. The machine code of the ANN model input to the controller of each neural processing unit may be configured to be processed in parallel in the plurality of neural processing units or may be compiled for parallel processing in the plurality of neural processing units. The memory controller may be configured to directly control a parallel processing of the plurality of neural processing units.

Other example specifics are included in the detailed description and drawings.

The present disclosure can accurately predict the onset probability and diagnosis result of cardiovascular disease through a device carried by a user. In particular, according to the present disclosure, personal sensing data, images of personal spaces, videos, and the like may not be shared in the cloud and transmission to a diagnosis server may be suppressed. Even in this case, the device itself can accurately predict the onset probability and diagnosis result of cardiovascular disease.

In addition, the present disclosure may secure digital biomarkers for diagnosis of a cardiovascular disease and provide solutions for diagnosis or prevention of diseases.

In addition, the present disclosure can effectively process various sensing data through a concatenation operation and a skip-connection operation. Accordingly, the present disclosure can rapidly and accurately predict a cardiovascular disease.

In addition, the present disclosure can control a neural processing unit for implementing a cardiovascular disease prediction model to operate more efficiently.

Accordingly, the present disclosure can reduce power consumption even when processing a huge amount of data. Therefore, according to the present disclosure, even in a small edge device having a small battery capacity, it is possible to predict the probability of occurrence of a user's cardiovascular disease. In particular, the present disclosure can determine an appropriate treatment intervention time by predicting the onset probability of a cardiovascular disease in daily life.

In addition, according to the present disclosure, data stored in an on-chip memory can be maximally reused to minimize power consumption while acquiring data necessary for predicting the onset probability of cardiovascular disease from an external memory.

Effects according to the present disclosure are not limited by the contents exemplified above, and various effects are included within the present disclosure.

BRIEF DESCRIPTION OF THE DRAWINGS

FIG. 15B is an exemplary diagram illustrating locality information of artificial neural network data of the artificial neural network model for predicting cardiovascular disease shown in FIG. 15A.

DETAILED DESCRIPTION OF THE EMBODIMENT

Figure 1:
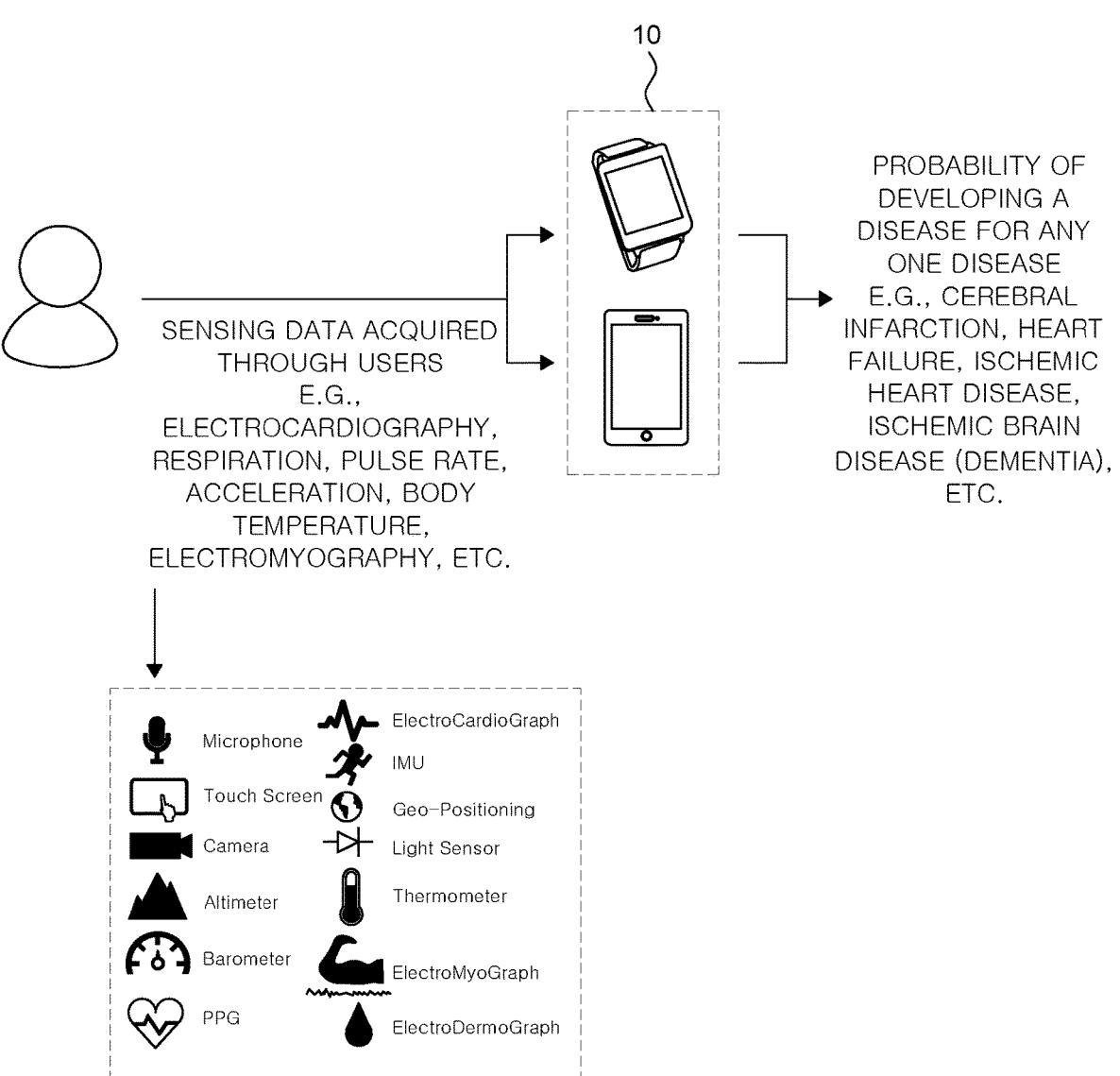
FIG. 1 is a schematic conceptual diagram illustrating an artificial neural network model for predicting a cardiovascular disease according to an example of the present disclosure.

Advantages and features of the present disclosure, and methods of achieving them, will become apparent with reference to the examples described below in detail in conjunction with the accompanying drawings. However, the present disclosure is not limited to the examples disclosed below and will be implemented in various different forms. These examples are provided so that the present disclosure is complete, and to fully inform those of ordinary skill in the art to which the present disclosure belongs, the scope of the present disclosure. The present disclosure is only defined by the scope of the claims. In connection with the description of the drawings, like reference numerals may be used for like elements.

In the present disclosure, expressions such as "have," "may have," "include," or "may include" indicate the presence of the corresponding feature (e.g., an element such as a numerical value, function, action, or part), and do not exclude the existence of the additional feature.

In the present disclosure, expressions such as "A or B," "at least one of A and/or B," or "one or more of A and/or B" may include all possible combinations of the items listed together. For example, "A or B," "at least one of A and B," or "at least one of A or B" may refer to all instances of (1) including at least one A, (2) including at least one B, or (3) including both at least one A and at least one B.

As used herein, expressions such as "first," "second," or "first or second," as used herein may modify various elements regardless of order and/or importance, and are used only to distinguish one element from another element, and do not limit the elements. For example, the first user device and the second user device may represent different user device regardless of order or importance. For example, without departing from the scope of the rights described in this document, the first element may be named as the second element, and similarly, the second element may also be renamed as the first element.

It should be understood that the certain element may be directly connected to the other element or may be connected through another element (e.g., a third element) when an element (e.g., first element) is referred to as being "(functionally or communicatively) connected with/to," "(operatively or communicatively) coupled with/to" or "in contact with (connected to)" another element (e.g., second element). On the other hand, it may be understood that no the other element (e.g., third element) exists between an element and another element when an element (e.g., first element) is referred to as being "directly connected to" or "directly in contact with" another element (e.g., second element).

The expression "configured to" used in the present disclosure may be used interchangeably with, for example, "suitable for," "having the capacity to," "designed to," "adapted to," "made to," or "capable of" depending on the situation. The term "configured (or configured to)" may not necessarily mean only "specifically designed to" in hardware. Instead, in some circumstances, the expression "a device configured to" may mean that the device is "capable of" with other devices or parts. For example, the phrase "a processor configured to (or configured to perform) A, B, and C" may mean a dedicated processor (e.g., an embedded processor) for performing the corresponding operation, or a generic-purpose processor (e.g., a CPU or an application processor) capable of performing corresponding operations by executing one or more software programs stored in the memory device.

Terms used in the present disclosure are used only to describe specific examples, and may not be intended to limit the scope of other examples. The singular expression may include the plural expression unless the context clearly dictates otherwise. Terms used herein, including technical or scientific terms, may have the same meanings as commonly understood by one of ordinary skill in the art described in this document. Among the terms used in this document, terms defined in a general dictionary may be interpreted with the same or similar meaning to the meaning in the context of the related art, and unless explicitly defined herein, it should not be construed in an idealistic or overly formal sense. In some cases, even terms defined in the present disclosure cannot be construed to exclude examples of this document.

Each feature of the various examples of the present disclosure may be partially or wholly combined or combined with each other, as those skilled in the art will fully understand, technically various interlocking and driving are possible, and each example may be implemented independently of each other or may be implemented together in a related relationship.

Hereinafter, in order to facilitate understanding of the disclosure presented in the present specification, terms used in the present specification will be briefly summarized.

NPU: an abbreviation of neural processing unit, which may refer to a processor specialized for computation of an ANN model separately from a central processing unit (CPU). ANN: an abbreviation of artificial neural network. In order to imitate human intelligence, it may refer to a network in which nodes are connected in a layer structure by mimicking those neurons in the human brain are connected through synapse.

For example, the artificial neural network (ANN) model for predicting cardiovascular disease can be models trained to perform inference such as object classification, object detection, object segmentation, image/video reconstruction, image/video enhancement, object tracking, event recognition, event prediction, anomaly detection, density estimation, event search, measurement and the like.

For example, the artificial neural network model may be a model such as Bisenet, Shelfnet, Alexnet, Densenet, Efficientnet, EfficientDet, Googlenet, Mnasnet, Mobilenet, Resnet, Shufflenet, Squeezenet, VGG, Yolo, RNN, CNN, DBN, RBM, LSTM and the like. However, the present disclosure is not limited thereto, and it may be a new artificial neural model other than those operable in the NPU 100.

Information on the structure of an artificial neural network includes information on the number of layers, the number of nodes in a layer, the value of each node, information on the calculation processing method, and information on the weight matrix applied to each node.

Information on the structure of an artificial neural network is information including information on the number of layers, the number of nodes in a layer, the value of each node, information on an operation processing method, and information on a weight matrix applied to each node.

Information on the data locality of the cardiovascular disease prediction artificial neural network model may be information including the order of data access requests to the memory determined based on the structure of the artificial neural network and the neural processing unit processing the artificial neural network.

DNN is an abbreviation of deep neural network, which may mean that the number of hidden layers of the ANN may be increased in order to implement higher artificial intelligence.

CNN is an abbreviation of convolutional neural network, which is a neural network that functions similar to image processing in the visual cortex of the human brain. Convolutional neural networks are known to be suitable for image processing, and are known to be superior to extract features from input data and identify patterns of features.

KERNEL may be the weight value of an N×M matrix for convolution.

The off-chip memory may be a memory arranged in consideration of a limited memory size inside the NPU. That is, a memory may be disposed outside the chip to store large-capacity data. The off-chip memory may include one of memories such as ROM, SRAM, DRAM, resistive RAM, magneto-resistive RAM, phase-change RAM, ferroelectric RAM, flash memory, high bandwidth memory (HBM), and the like. The off-chip memory may include at least one memory unit. The off-chip memory may be configured as a homogeneous memory unit or a heterogeneous memory unit.

The NPU may include on-chip memory. On-chip memory may include volatile memory and/or non-volatile memory. For example, the on-chip memory may include one of memories such as ROM, SRAM, DRAM, resistive RAM, magneto-resistive RAM, phase-change RAM, ferroelectric RAM, flash memory, high bandwidth memory (HBM), and the like. The on-chip memory may include at least one memory unit. The on-chip memory may be configured as a homogeneous memory unit or a heterogeneous memory unit.

Hereinafter, examples of the present disclosure will be described with reference to the accompanying drawings.

FIG. 1 illustrates an artificial neural network model for predicting cardiovascular disease according to an example of the present disclosure.

Referring to FIG. 1, an artificial neural network model for predicting cardiovascular disease may be performed in a user device 10 carried by a user. The user device 10 may obtain sensing data from the user in order to perform calculation of an artificial neural network model for predicting cardiovascular disease. The user device 10 may predict a disease onset probability for at least one disease by inputting the sensing data to an artificial neural network model for predicting cardiovascular disease.

For example, the user device 10 may obtain sensing data related to the user through a microphone, a touch screen, a camera, an altimeter, a barometer, a photoplethysmogram (PPG), an electrocardiogram (ECG), an inertial measurement unit (IMU), a geo-positioning system, a light sensor, a thermometer, an electromyograph (EMG), an electrodermograph (EDG), and the like built into the device.

The user device 10 may acquire, for example, a user's electrocardiography (ECG), respiration, pulse rate, acceleration, body temperature, electromyography, gait data (e.g., direction, number of steps, step length), face data, gaze data, and the like through a sensor built into the device.

Meanwhile, the user device 10 may additionally obtain data for analyzing and/or fusion of the user's sensing data from the user. For example, the user device 10 may obtain image data of a space where the user is located. As another example, in order to analyze the user's sleep, the user device 10 may obtain sensing data in major sleep/non-sleep states, such as activity level, brightness, pulse rate, time zone, and bedtime. Furthermore, the user device 10 may additionally obtain data such as date, name, gender, age, time of waking up, time of sleep the previous day, quality of sleep the previous day, degree of refreshment on the day, duration of not wearing the wearable device, amount of caffeine intake, amount of alcohol intake, daytime nap, and BMI from the user. As another example, the user device 10 may additionally acquire data such as cardiovascular disease-related factors (e.g., height, weight, blood pressure, waist circumference, BMI, visual acuity, muscle mass, body fat, visceral fat, skeletal muscle mass, total cholesterol, triglyceride, HDL cholesterol, and LDL cholesterol) through a user or an external on-chip memory. As another example, the user device 10 may additionally obtain past health checkup data, past questionnaire item data, and past medical record data for the user through databases of medical institutions and medical insurance providers.

The user device 10 may predict the onset probability of diseases that may occur in old age, such as cerebral infarction, heart failure, ischemic heart disease, and ischemic brain disease, by inputting the above-described sensing data to the cardiovascular disease prediction artificial neural network model. For example, the user device 10 may input at least two types of sensing data as described above to predict the onset probability of at least two diseases. Here, predicting the onset probability of a disease by the user device 10 may be understood as predicting the onset probability at a current time point and the onset probability at a predetermined time point. For example, the predetermined point in time may be a point in the future or a point in the past based on the current point in time.

In another example, the user device 10 may calculate the current state of the user with respect to the disease as at least one of a population-to-population health rank, a percentile, and a score based on the incidence probability at the current time point and the incidence probability at a predetermined time point. Here, the health rank and percentile relative to the population may be numerical values indicating the rank of the health status of the user relative to the population or the percentage of the user based on the percentile relative to the population. Also, the score may be, for example, a numerical value indicating a score for the user's health condition on a scale of 100 points.

In another example, the user device 10 may predict the onset of a disease through an artificial neural network model for predicting cardiovascular disease, and may predict a survival rate within a predetermined period after the onset of the disease.

In the case of a cardiovascular disease prediction artificial neural network model, user's sensing data (e.g., biometric data, user motion data) can be learned as cohort data tracking changes in the user's disease symptoms and disease onset patterns. For example, an artificial neural network model for predicting cardiovascular disease may be trained using a random forest as an ensemble model.

Meanwhile, ischemic brain disease that the user device 10 may predict through an artificial neural network model for predicting cardiovascular disease may include hypoxic-ischemic encephalopathy (HIE), stroke, cerebral infarction, cerebral ischemia, thrombosis, embolism, transient ischemic attack, lacunes, head trauma, cerebral circulation metabolic disorder, cerebral functional coma, traumatic brain injury, vascular dementia, Alzheimer's dementia, Huntington's disease, and Parkinson's disease.

On the other hand, the user device 10 according to an example of the present disclosure may be a device capable of collecting data for diagnosing a cardiovascular disease and displaying a diagnosis result. For example, the user device 100 may include, but is not limited to, a wearable device (e.g., smart watch, smart glasses, etc.), a smartphone, and the like that can be worn on a user's body part.

Hereinafter, a user device 10 that performs an operation of an artificial neural network model for predicting cardiovascular disease will be described.

Figure 2:
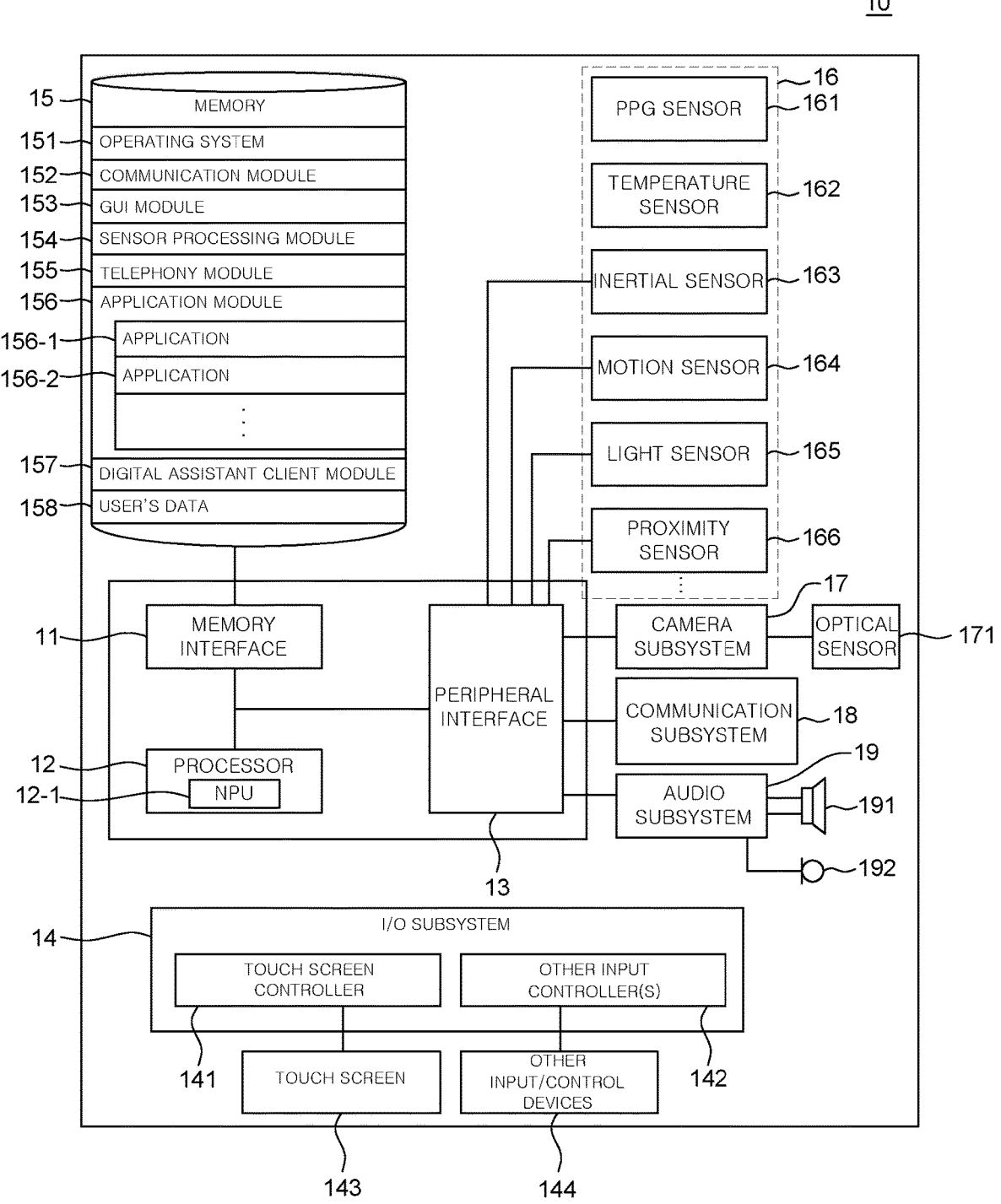
FIG. 2 is a conceptual diagram illustrating a user device including a neural processing unit for an artificial neural network model for predicting a cardiovascular disease according to an example of the present disclosure.

FIG. 2 illustrates a user device including a neural processing unit for an artificial neural network model for predicting cardiovascular disease according to an example of the present disclosure.

Referring to FIG. 2, the user device 10 may include a memory interface 11, one or more processors 12, and a peripheral interface 13. The various components within the user device 10 may be connected by one or more communication buses or signal lines.

The memory interface 11 may be connected to the memory 15 and transfer various data to the processor 12. Here, the memory 15 is a memory mounted on a semiconductor die and may be a memory for caching or storing data processed by the user device 10. The memory 15 may include one of memories such as ROM, SRAM, DRAM, resistive RAM, magneto-resistive RAM, phase-change RAM, ferroelectric RAM, flash memory, high bandwidth memory (HBM), and the like. The memory 15 may include at least one memory unit. The memory 15 may be configured as a homogeneous memory unit or a heterogeneous memory unit.

In various examples, the memory 15 may store at least one of an operating system 151, a communication module 152, a graphical user interface module (GUI) 153, a sensor processing module 154, a phone module 155, and an application 156. Specifically, the operating system 151 may include instructions for processing basic system services and instructions for performing hardware tasks. The communication module 152 may communicate with one or more other devices, computers, and servers. The GUI 153 may process a graphical user interface. The sensor processing module 154 may process sensor-related functions; for example, it may process a voice input received using one or more microphones 192. The phone module 155 may process phone-related functions. The application module 156 may perform various functions of a user application, such as electronic messaging, web browsing, media processing, navigation, imaging, and other processing functions. In addition, the user device 10 may store one or more software applications 156-1 and 156-2 associated with any one type of service (e.g., an application for user disease care and the like) in the memory 15.

In various examples, the memory 15 may store a digital assistant (DA) client module 157, and thus the memory 15 may store commands for performing client-side functions of the digital assistant and various user data 158.

Meanwhile, the DA client module 157 may obtain a user's voice input, text input, touch input, and/or gesture input through various user interfaces (e.g., the I/O subsystem 14) provided in the user device 10.

In addition, the DA client module 157 may output audio-visual and tactile data. For example, the DA client module 157 may output data including a combination of at least two of voice, sound, notification, text message, menu, graphics, video, animation, and vibration. In addition, the DA client module 157 may communicate with a digital assistant server using a communication subsystem 18.

In various examples, the DA client module 157 may collect additional information about the surrounding environment of user device 10 from various sensors, subsystems, and peripheral devices to construct a context associated with user input. For example, the DA client module 157 may infer the user's intention by providing context information together with the user's input to the digital assistant server. Here, the context information that may accompany the user input may include sensor information, e.g., lighting, ambient noise, ambient temperature, image of the surrounding environment, video, and the like. For another example, the context information may include the physical state of the user device 10 (e.g., device orientation, device location, device temperature, power level, speed, acceleration, motion patterns, cellular signal strength, and the like). For another example, the context information may include information related to the software state of the user device 10 (e.g., processes running on the user device 10, installed programs, past and current network activity, background services, error logs, resource usage, and the like).

In various examples, the memory 15 may include added or deleted commands, and the user device 10 may also include additional components other than those shown in FIG. 2 or may exclude some components.

The processor 12 may control the overall operation of the user device 10. The processor 12 may correspond to an arithmetic device such as a central processing unit (CPU) or an application processor (AP). For example, the processor 200 may be a micro processing unit (MPU) or a micro controller unit (MCU).

In various examples, the processor 12 may be a neural processing unit (NPU) 12-1, and the processor 12 may be implemented in the form of an integrated chip (IC) such as a system on chip (SoC) in which various computing devices such as the NPU 12-1, CPU, and GPU are integrated.

In various examples, when the processor 12 is the NPU 12-1 or is configured to include the NPU 12-1, the processor 12 may have computing power capable of processing the cardiovascular disease prediction artificial neural network model in real time.

To elaborate, since the artificial neural network model for predicting cardiovascular disease has a data-intensive computational characteristic, the processor 12 may include the NPU 12-1 for processing inference operations of 30 frames per second or more. However, examples of the present disclosure are not limited to NPUs.

The peripheral interface 13 may be connected to various sensors, subsystems, and peripheral devices to provide data so that the user device 10 can perform various functions. Here, that the user device 10 performs a certain function may be understood as being performed by the processor 12.

The peripheral interface 13 may receive data from a plurality of sensors 16. In one example, the peripheral interface 13 may receive data from the ECG sensor 161, the temperature sensor 162, the inertial sensor 163, the motion sensor 164, the light sensor 165, and the proximity sensor 166. However, the sensors 16 may further include data necessary for predicting cardiovascular disease, in addition to the sensor shown in FIG. 2.

In various examples, user device 10 may include camera subsystem 17 coupled with the peripheral interface 13 and an optical sensor 171 coupled therewith. Through this, the user device 10 can perform various recording functions such as taking pictures and recording video clips.

In various examples, the user device 10 may include the communication subsystem 18 coupled with the peripheral interface 13. The communication subsystem 18 is composed of one or more wired/wireless networks, and may include various communication ports, radio frequency transceivers, and optical transceivers.

In various examples, the user device 10 may include an audio subsystem 19 coupled with the peripheral interface 13. The audio subsystem 19 includes one or more speakers 191 and one or more microphones 192, so that the user device 10 may perform voice-activated functions, such as voice recognition, voice replication, digital recording, and telephony functions.

In various examples, the user device 10 may include an I/O subsystem 14 coupled with the peripheral interface 13. For example, the I/O subsystem 14 may control a touch screen 143 included in the user device 10 through a touch screen controller 141. As an example, the touch screen controller 141 may detect the user's touch and movement or the cessation of the touch and movement using any one of a plurality of touch sensing technologies such as capacitive, resistive, infrared, surface acoustic wave (SAW) technology, a proximity sensor array, and the like. As another example, the I/O subsystem 14 may control other input/control devices 144 included in the user device 10 via other input controller(s) 142. As an example, other input controller(s) 142 may control one or more buttons, rocker switches, thumb-wheels, infrared ports, USB ports, and pointer devices such as styluses and the like. Hereinafter, a neural processing unit (NPU) 12-1 included in or corresponding to the processor 12 of the user device 10 will be described.

Figure 3:
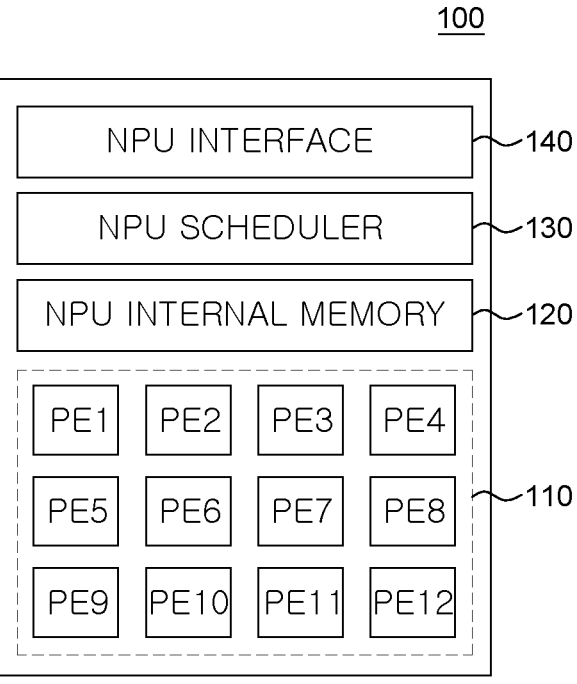
FIG. 3 is a schematic conceptual diagram illustrating a neural processing unit according to the present disclosure.

FIG. 3 illustrates a neural processing unit according to the present disclosure.

Prior to describing FIG. 3, it may be understood that the neural processing unit (NPU) 100 may have the same configuration as the NPU 12-1 included in the user device 10. Specifically, the NPU 100 is a processor specialized to perform an operation for an artificial neural network model for predicting cardiovascular disease.

An artificial neural network refers to a network of artificial neurons that multiplies and adds weights when multiple inputs or stimuli are received, and that transforms and transmits the value added with an additional deviation through an activation function. The trained artificial neural network can be used to output inference results from input data.

The NPU 100 may be a semiconductor implemented as an electric/electronic circuit. The electric/electronic circuit may include number of electronic devices (e.g., a transistor and a capacitor).

Referring to FIG. 3, the NPU 100 may include a processing element (PE) array 110, an NPU internal memory 120, an NPU scheduler 130, and an NPU interface 140. Each of the processing element array 110, the NPU internal memory 120, the NPU scheduler 130, and the NPU interface 140 may be a semiconductor circuit to which numerous transistors are connected. Therefore, some of them may be difficult to identify and distinguish with the naked eye, and may be identified only by an operation. For example, a specific circuit may operate as the processing element array 110, or may operate as the NPU scheduler 130. The NPU scheduler 130 may be configured to perform the function of the controller configured to control the artificial neural network inference operation of the NPU 100. To elaborate, a part of the controller may be referred to as the scheduler 130. The NPU scheduler 130 may be part of the controller. The NPU scheduler 130 may also be referred to as a controller. The controller may include the NPU scheduler 130. The controller may be a common name for circuits that perform various control functions of the NPU 100. It is also possible that the controller is defined by the function of the circuit. In other words, the NPU scheduler 130 may be defined as a component in which the controller controls the order of each operation step of the artificial neural network model based on the locality of the artificial neural network data of the artificial neural network model.

The NPU 100 may include a processing element array 110, an NPU internal memory 120 configured to store a cardiovascular disease prediction artificial neural network model that can be inferred by the processing element array 110, and a NPU scheduler 130 configured to control the processing element array 110 and the NPU internal memory 120 based on the data locality information or information about the structure of the cardiovascular disease prediction artificial neural network model. Here, the cardiovascular disease prediction artificial neural network model may include information on data locality information or structure of the cardiovascular disease prediction artificial neural network model. That is, the cardiovascular disease prediction artificial neural network model may refer to an AI recognition model trained to perform a specific inference function (e.g., probability of developing the disease).

The processing element array 110 may perform an operation for an artificial neural network.

The NPU interface 140 may communicate with various components connected to the NPU 100 through a system bus (one or more communication buses or signal lines), for example, a memory.

The NPU scheduler 130 may be configured to control the operation of the processing element array 110 for the inference operation of the neural processing unit 100 and the sequence of the read operation and the write operation of the NPU internal memory 120.

The NPU scheduler 130 may be configured to control the processing element array 110 and the NPU internal memory 120 based on the data locality information or information about the structure of the cardiovascular disease prediction artificial neural network model.

The NPU scheduler 130 may analyze the structure of the cardiovascular disease prediction artificial neural network model to be operated in the processing element array 100 or may receive the pre-analyzed information. For example, the data of the artificial neural network that can be included in a cardiovascular disease prediction artificial neural network model may include at least a portion of node data (i.e., feature map) of each layer, arrangement data of layers, locality information or structure information, and weight data of each connection network (i.e., weight kernel) connecting nodes of each layer. The data of the artificial neural network may be stored in a memory provided inside the NPU scheduler 130 or the NPU internal memory 120.

The NPU scheduler 130 may schedule the operation sequence of the cardiovascular disease prediction artificial neural network model to be performed by the NPU 100 based on the data locality information or the structure information of the cardiovascular disease prediction artificial neural network model. Machine code may include scheduling data. The NPU scheduler 130 may operate according to scheduling included in the machine code.

The NPU scheduler 130 may acquire a memory address value, in which the feature map and weight data of the layer of the cardiovascular disease prediction artificial neural network model are stored, based on the data locality information or the structure information of the cardiovascular disease prediction artificial neural network model. For example, the NPU scheduler 130 may obtain a memory address value in which the feature map and weight data of the layer of the cardiovascular disease prediction artificial neural network model stored in the memory. Therefore, the NPU scheduler 130 may transmit the feature map and weight data of the layer of the cardiovascular disease prediction artificial neural network model to be driven from the memory 200 and store it in the NPU internal memory 120.

The feature map of each layer may have a corresponding memory address value, respectively.

Each weight data may have a corresponding memory address value, respectively.

The NPU scheduler 130 may schedule an operation sequence of the processing element array 110 based on the data locality information or the information about the structure of the cardiovascular disease prediction artificial neural network model, for example, the data locality information of a layout of layers of the cardiovascular disease prediction artificial neural network or the information about the structure of the cardiovascular disease prediction artificial neural network model.

The NPU scheduler 130 may schedule based on the data locality information or the information about the structure of the cardiovascular disease prediction artificial neural network model so that the NPU scheduler may operate in a different way from a scheduling concept of a conventional CPU. The scheduling of the conventional CPU operates to provide the highest efficiency in consideration of fairness, efficiency, stability, and reaction time. That is, the conventional CPU schedules to perform the most processing during the same time in consideration of a priority and an operation time.

A conventional CPU uses an algorithm which schedules a task in consideration of data such as a priority or an operation processing time of each processing.

In contrast, the NPU scheduler 130 may determine a processing sequence based on the data locality information or the information about the structure of the cardiovascular disease prediction artificial neural network model.

Moreover, the NPU scheduler 130 may operate the NPU 100 according to the determined processing sequence based on the data locality information or the information about the structure of the cardiovascular disease prediction artificial neural network model and/or data locality information or information of an NPU 100.

However, the present disclosure is not limited to the data locality information or the information about the structure of the NPU 100.

NPU scheduler 130 may be configured to store information about the data locality information or structure of the artificial neural network.

That is, the NPU scheduler 130 may determine the processing sequence even if only information on the data locality information or structure of the cardiovascular disease prediction artificial neural network model is provided.

Furthermore, the NPU scheduler 130 may determine the processing sequence of the NPU 100 in consideration of the information on the data locality information or structure of the cardiovascular disease prediction artificial neural network model and the data locality information or information on the structure of the NPU 100. In addition, it is also possible to optimize the processing of the NPU 100 in the determined processing sequence.

The processing element array 110 may refer to a configuration in which a plurality of processing elements PE1 to PE12 configured to calculate the feature map and weight data of the artificial neural network are disposed. Each processing element may include a multiply and accumulate (MAC) operator and/or an arithmetic logic unit (ALU) operator. However, examples according to the present disclosure are not limited thereto.

Although FIG. 3 shows a plurality of processing elements, it is also possible to configure operators implemented as a plurality of multipliers and adder trees to be arranged in parallel by replacing the MAC in one processing element. In this case, the processing element array 110 may be referred to as at least one processing element including a plurality of operators.

The processing element array 110 is configured to include a plurality of processing elements PE1 to PE12. The plurality of processing elements PE1 to PE12 shown in FIG. 1 is merely an example for convenience of description, and the number of the plurality of processing elements PE1 to PE12 is not limited thereto. The size or number of the processing element array 110 may be determined by the number of the plurality of processing elements PE1 to PE12. The size of the processing element array 110 may be implemented in the form of an N×M matrix. Here, N and M are integers greater than zero. The processing element array 110 may include N×M processing elements. That is, there may be at least one processing element.

The size of the processing element array 110 may be designed in consideration of the characteristics of the cardiovascular disease prediction artificial neural network model in which the NPU 100 operates.

The processing element array 110 may be configured to perform functions such as addition, multiplication, and accumulation required for an artificial neural network operation. In other words, the processing element array 110 may be configured to perform a multiplication and accumulation (MAC) operation.

The processing element array 110 may be configured to quantize and output MAC operation results. However, examples of the present disclosure are not limited thereto.

The NPU internal memory 120 may store all or a portion of the cardiovascular disease prediction artificial neural network model according to the memory size and the data size of the cardiovascular disease prediction artificial neural network model.

Hereinafter, the first processing element PE1 of the processing element array 110 will be described as an example.

Figure 4:
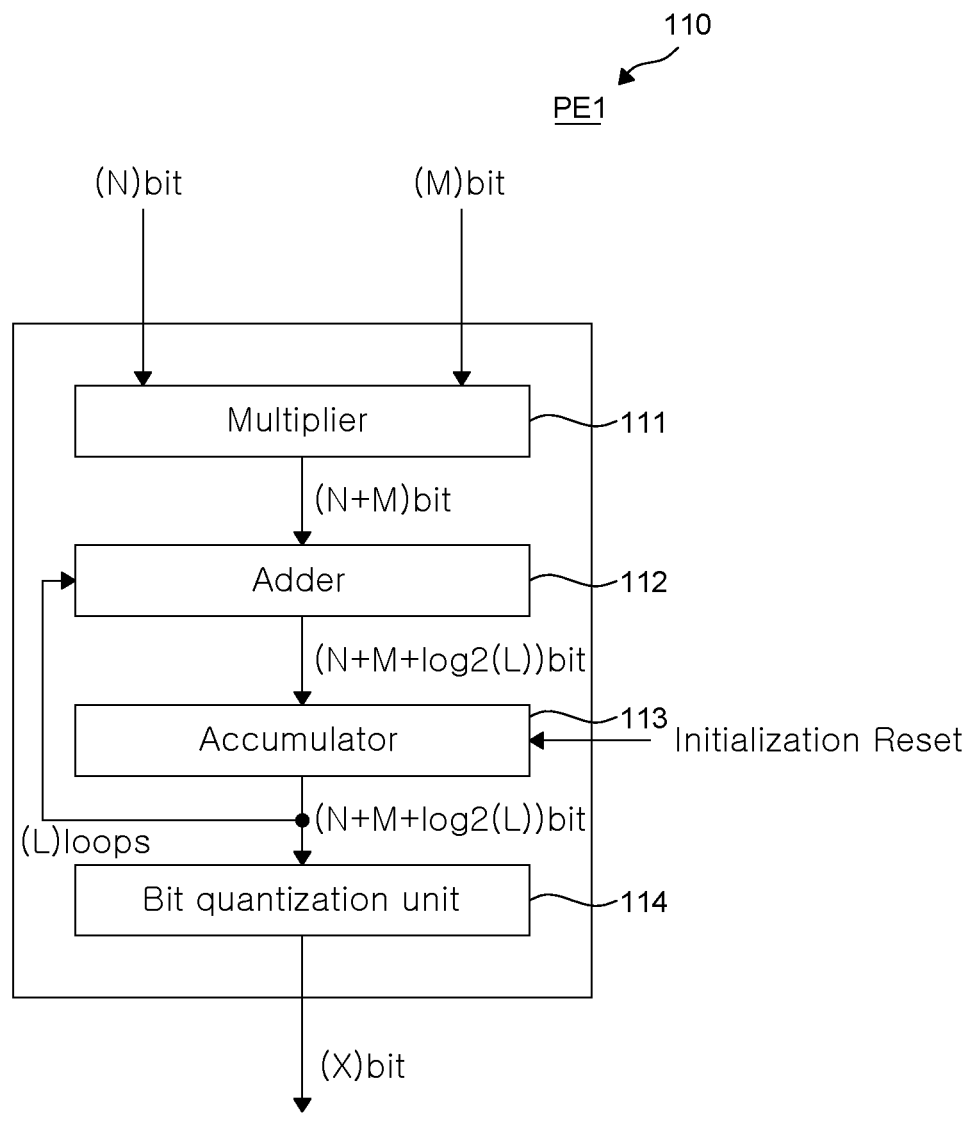
FIG. 4 is a schematic conceptual diagram illustrating one processing element of the array of processing elements shown in FIG. 3.

FIG. 4 illustrates one processing element of the array of processing elements shown in FIG. 3.

Referring to FIG. 4, the first processing element PE1 may be configured to include a multiplier 111, an adder 112, an accumulator 113, and a bit quantization unit 114. However, examples according to the present disclosure are not limited thereto, and the processing element array 110 may be modified in consideration of the computational characteristics of the artificial neural network.

The multiplier 111 multiplies the received (N) bit data and (M) bit data. The operation value of the multiplier 111 is output as (N+M) bit data.

The multiplier 111 may be configured to receive one variable and one constant.

The accumulator 113 may accumulate the operation value of the multiplier 111 and the operation value of the accumulator 113 by using the adder 112 for a number of L loops. Accordingly, the number of bits of data in the output unit and the input unit of the accumulator 113 may be output as (N+M+log 2(L)) bits, where L is an integer greater than zero. When the accumulation is finished, the accumulator 113 may receive an initialization reset to initialize the data stored in the accumulator 113 to zero. However, examples according to the present disclosure are not limited thereto.

The bit quantization unit 114 may reduce the number of bits of data output from the accumulator 113. The bit quantization unit 114 may be controlled by the NPU scheduler 130. The number of bits of the quantized data may be output as X bits, where X is an integer greater than zero. According to the above configuration, the processing element array 110 is configured to perform a MAC operation, and the processing element array 110 has an effect of quantizing and outputting the MAC operation result. In particular, such quantization has the effect of further reducing power consumption as the number of L loops increases. In addition, if the power consumption is reduced, there is an effect that the heat generation of the edge device can also be reduced. In particular, reducing heat generation has an effect of reducing the possibility of malfunction due to high temperature of the neural processing unit 100.

The output data X bit of the bit quantization unit 114 may be node data of a next layer or input data of convolution. If the cardiovascular disease prediction artificial neural network model has been quantized, the bit quantization unit 114 may be configured to receive quantized information from the cardiovascular disease prediction artificial neural network model. However, it is not limited thereto, and the NPU scheduler 130 may be configured to extract quantized information by analyzing the cardiovascular disease prediction artificial neural network model. Therefore, the output data X bits may be converted into the quantized number of bits to correspond to the quantized data size and output. The output data X bit of the bit quantization unit 114 may be stored in the NPU internal memory 120 as the number of quantized bits.

That is, the processing element array 110 of the NPU 100 according to an example of the present disclosure may include a multiplier 111, an adder 112, an accumulator 113, and a bit quantization unit 114.

Hereinafter, another example of the NPU 100 of the present disclosure will be described.

Figure 5:
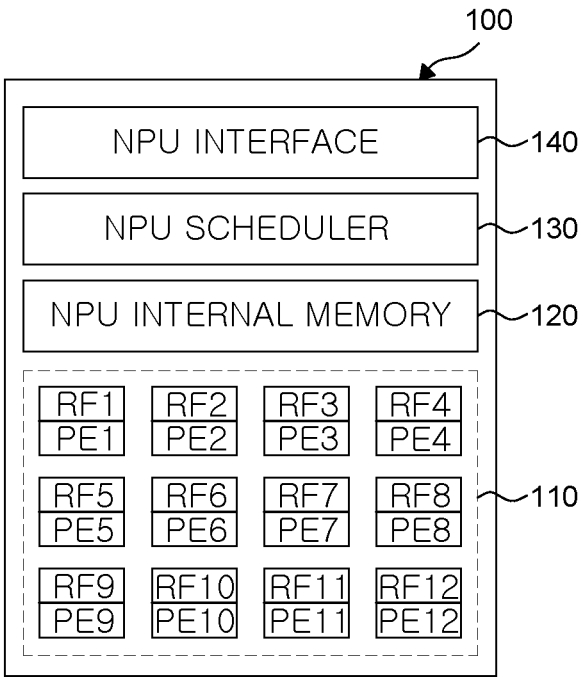
FIG. 5 is a conceptual diagram illustrating a modified example of the neural processing unit shown in FIG. 3.

FIG. 5 shows a modified example of the NPU 100 shown in FIG. 3.

Since the NPU 100 shown in FIG. 5 is substantially the same as the NPU 100 exemplified in FIG. 3, except for the processing element array 110, hereinafter, redundant description may be omitted for convenience of description.

The processing element array 110 of FIG. 5 may be configured to further include a plurality of processing elements PE1 to PE12 and respective register files RF1 to RF12 corresponding to each of the processing elements PE1 to PE12.

The plurality of processing elements PE1 to PE12 and the plurality of register files RF1 to RF12 as illustrated in FIG. 3 are merely examples for convenience of description, and the number of the plurality of processing elements PE1 to PE12 and the plurality of register files RF1 to RF12 is not limited thereto.

The size or number of the processing element array 110 may be determined by the number of the plurality of processing elements PE1 to PE12 and the plurality of register files RF1 to RF12. The size of the processing element array 110 and the plurality of register files RF1 to RF12 may be implemented in the form of an N×M matrix, where N and M are integers greater than zero.

The array size of the processing element array 110 may be designed in consideration of the characteristics of the cardiovascular disease prediction artificial neural network model in which the NPU 100 operates. In other words, the memory size of the register file may be determined in consideration of the data size of the artificial neural network model to be operated, the required operating speed, the required power consumption, and the like.

The register files RF1 to RF12 of the NPU 100 are static memory units directly connected to the processing elements PE1 to PE12. The register files RF1 to RF12 may include, for example, flip-flops and/or latches. The register files RF1 to RF12 may be configured to store MAC operation values of the corresponding processing elements RF1 to RF12. The register files RF1 to RF12 may be configured to provide or receive weight data and/or node data to the NPU internal memory 120.

It is also possible that the register files RF1 to RF12 are configured to perform a function of a temporary memory of the accumulator during MAC operation.

Hereinafter, calculation of an exemplary artificial neural network model 110-10 for predicting cardiovascular disease that can be operated in the NPU 100 will be described.

Figure 6:
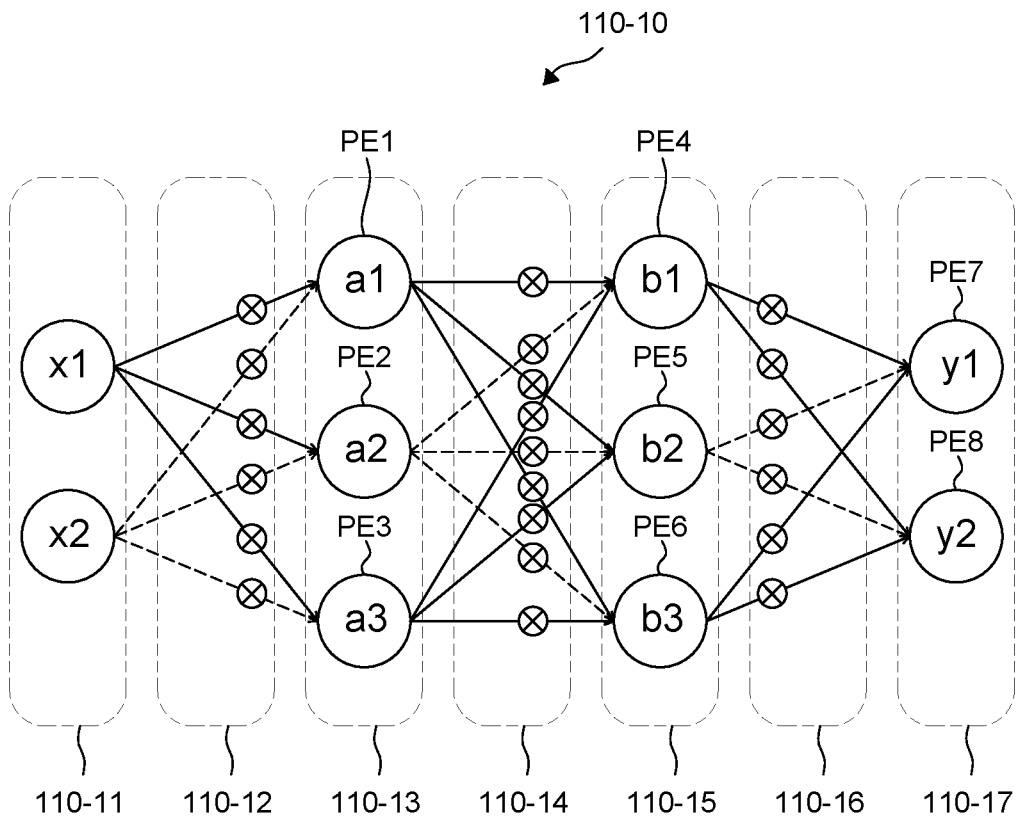
FIG. 6 is a schematic conceptual diagram illustrating an exemplary cardiovascular disease prediction artificial neural network model.

FIG. 6 illustrates an exemplary cardiovascular disease prediction artificial neural network model.

The exemplary cardiovascular disease prediction artificial neural network model 110-10 of FIG. 6 may be an artificial neural network trained by the NPU 100 or trained by the device illustrated in FIG. 3 or FIG. 5 or a separate machine learning device. The cardiovascular disease prediction artificial neural network model 110-10 may be an artificial neural network trained to perform various inference functions, such as object recognition and voice recognition.

The cardiovascular disease prediction artificial neural network model 110-10 may be a deep neural network (DNN). However, the cardiovascular disease prediction artificial neural network model 110-10 according to examples of the present disclosure is not limited to a deep neural network.

For example, the cardiovascular disease prediction artificial neural network model may be a model to be trained to perform inference such as object detection, object segmentation, image/video reconstruction, image/video enhancement, object tracking, event recognition, event prediction, anomaly detection, density estimation, event search, measurement, and the like.

For example, the cardiovascular disease prediction artificial neural network model can be a model such as Bisenet, Shelfnet, Alexnet, Densenet, Efficientnet, EfficientDet, Googlenet, Mnasnet, Mobilenet, Resnet, Shufflenet, Squeezenet, VGG, Yolo, RNN, CNN, DBN, RBM, LSTM, and the like. However, the present disclosure is not limited thereto, and a novel artificial neural network model to operate in the NPU 100 has been continuously released.

In various examples, the cardiovascular disease prediction artificial neural network model 110-10 may be an ensemble model based on at least two different models.

The cardiovascular disease prediction artificial neural network model 110-10 may be stored in the NPU internal memory 120 of the NPU 100.

Specifically, referring to FIG. 4, the inference process of the cardiovascular disease prediction artificial neural network model 110-10 may be performed by the NPU 100.

The cardiovascular disease prediction artificial neural network model 110-10 may be an exemplary deep neural network model configured to include an input layer 110-11, a first connection network 110-12, a first hidden layer 110-13, a second connection network 110-14, a second hidden layer 110-15, a third connection network 110-16, and an output layer 110-17. However, the present disclosure is not limited to the cardiovascular disease prediction artificial neural network model illustrated in FIG. 6. The first hidden layer 110-13 and the second hidden layer 110-15 may be referred to as a plurality of hidden layers.

The input layer 110-11 may include, for example, x1 and x2 input nodes. That is, the input layer 110-11 may include node data including two node values. The NPU scheduler 130 illustrated in FIG. 3 or FIG. 5 may set a memory address in which the input data of the input layer 110-11 is stored in the NPU internal memory 120 illustrated in FIG. 3 or FIG. 5.

The first connection network 110-12 may include, for example, connections having weight value including six weight values connecting each node of the input layer 110-11 and each node of the first hidden layer 110-13. The NPU scheduler 130 illustrated in FIG. 3 or FIG. 5 may set a memory address in which the weight value of the first connection network 110-12 is stored in the NPU internal memory 120. Each weight value is multiplied with each input node value, and an accumulated value of the multiplied values is stored in the first hidden layer 110-13. Here, the nodes may be referred to as the feature map.

The first hidden layer 110-13 may include, for example, nodes a1, a2, and a3. That is, the first hidden layer 110-13 may include node data including three node values. The NPU scheduler 130 illustrated in FIG. 3 or FIG. 5 may set a memory address in which the node value of the first hidden layer 110-13 is stored in the NPU internal memory 120.

The NPU scheduler 130 may be configured to schedule an operation sequence so that the first processing element PE1 performs the MAC operation of the a1 node of the first hidden layer 110-13. The NPU scheduler 130 may be configured to schedule the operation sequence so that the second processing element PE2 performs the MAC operation of the a2 node of the first hidden layer 110-13. The NPU scheduler 130 may be configured to schedule an operation sequence so that the third processing element PE3 performs the MAC operation of the a3 node of the first hidden layer 110-13. Here, the NPU scheduler 130 may pre-schedule the operation sequence so that the three processing elements perform each MAC operation simultaneously in parallel. The scheduling information may be included in machine code.

The second connection network 110-14 may include, for example, connections having weight value including nine weight values connecting each node of the first hidden layer 110-13 and each node of the second hidden layer 110-15. The NPU scheduler 130 illustrated in FIG. 3 or FIG. 5 may set a memory address in which the weight value of the second connection network 110-14 is stored in the NPU internal memory 120. The weight value of the second connection network 110-14 is multiplied by the input node value of the first hidden layer 110-13, respectively, and the accumulated value of the multiplied values is stored in the second hidden layer 110-15.

The second hidden layer 110-15 may include, for example, nodes b1, b2, and b3. That is, the second hidden layer 110-15 may include information with respect to the three node values. The NPU scheduler 130 may set a memory address for storing information on node value of the second hidden layer 110-15 in the NPU internal memory 120.

The NPU scheduler 130 may be configured to schedule an operation sequence so that the fourth processing element PE4 performs the MAC operation of the b1 node of the second hidden layer 110-15. The NPU scheduler 130 may be configured to schedule an operation sequence so that the fifth processing element PE5 performs the MAC operation of the b2 node of the second hidden layer 110-15. The NPU scheduler 130 may be configured to schedule an operation sequence so that the sixth processing element PE6 performs the MAC operation of the b3 node of the second hidden layer 110-15. The scheduling information may be included in machine code.

Here, the NPU scheduler 130 may pre-schedule the operation sequence so that the three processing elements perform each MAC operation simultaneously in parallel.

Here, the NPU scheduler 130 may determine scheduling so that the operation of the second hidden layer 110-15 will be performed after the MAC operation of the first hidden layer 110-13 of the cardiovascular disease prediction artificial neural network model.

That is, the NPU scheduler 130 may be configured to control the processing element array 100 and the NPU internal memory 120 based on the data locality information or structure information of the cardiovascular disease prediction artificial neural network model.

The third connection network 110-16 may include, for example, information on six weight values connecting each node of the second hidden layer 110-15 and each node of the output layer 110-17. The NPU scheduler 130 may set a memory address for storing the weight value of the third connection network 110-16 in the NPU internal memory 120. Weight value of the third connection network 110-16 is multiplied by the input node value of the second hidden layer 110-15, and the accumulated value of the multiplied values is stored in the output layer 110-17.

The output layer 110-17 may include, for example, y1 and y2 nodes. That is, the output layer 110-17 may include information with respect to the two node values. The NPU scheduler 130 may set a memory address for storing information on the node value of the output layer 110-17 in the NPU internal memory 120.

The NPU scheduler 130 may be configured to schedule the operation sequence so that the seventh processing element PE7 performs the MAC operation of the y1 node of the output layer 110-17. The NPU scheduler 130 may be configured to schedule the operation sequence so that the eighth processing element PE8 performs the MAC operation of the y2 node of the output layer 110-15. The scheduling information may be included in machine code. Here, the NPU scheduler 130 may pre-schedule the operation sequence so that the two processing elements perform each MAC operation simultaneously in parallel.

Here, the NPU scheduler 130 may determine the scheduling so that the operation of the output layer 110-17 will be performed after the MAC operation of the second hidden layer 110-15 of the artificial neural network model.

That is, the NPU scheduler 130 may be configured to control the processing element array 100 and the NPU internal memory 120 based on the data locality information or structure information of the cardiovascular disease prediction artificial neural network model.

That is, the NPU scheduler 130 may analyze or receive the structure of a cardiovascular disease prediction artificial neural network model to operate in the processing element array 110. The artificial neural network data that the cardiovascular disease prediction artificial neural network model can include may include a node value of each layer, information on the locality information or structure of the layout data of the layers or information on the weight value of each network connecting the nodes of each layer.

As the NPU scheduler 130 is provided with structure data or artificial neural network data locality information of the exemplary cardiovascular disease prediction neural network model 110-10, the NPU scheduler 130 is also capable of analyzing the operation sequence from the input to the output of the cardiovascular disease prediction artificial neural network model 110-10.

Accordingly, the NPU scheduler 130 may set the memory address in which the MAC operation values of each layer are stored in the NPU internal memory 120 in consideration of the scheduling sequence.

The NPU internal memory 120 may be configured to preserve the weight data of the connections stored in the NPU internal memory 120 while the inference operation of the NPU 100 is continued. Accordingly, there is an effect of reducing a number of memory read/write operations.

That is, the NPU internal memory 120 may be configured to reuse the MAC operation value stored in the NPU internal memory 120 while the inference operation is continued.

Hereinafter, the structure of the artificial neural network model for predicting cardiovascular disease according to the present disclosure will be described with reference to FIGS. 7 to 10.

Figure 7:
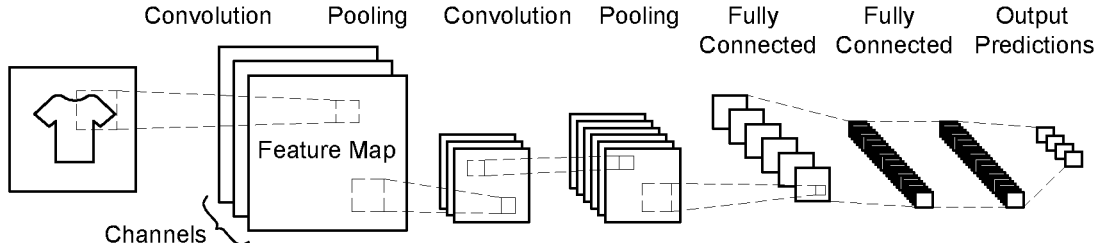
FIG. 7 is a diagram for explaining the basic structure of a cardiovascular disease prediction artificial neural network model.

FIG. 7 shows a basic structure of a convolutional neural network constituting an artificial neural network model for predicting cardiovascular disease according to an example of the present disclosure.

Referring to FIG. 7, a convolutional neural network may be a combination of at least one convolutional layer, a pooling layer, and a fully connected layer. The convolutional neural network has a structure suitable for learning and inference of two-dimensional data, and can be trained through a backpropagation algorithm.

In the example of the present disclosure, in the convolutional neural network, a kernel for extracting features of an input image of a channel for each channel may be provided. The kernel may be composed of a two-dimensional matrix, and convolution operation may be performed while traversing input data. The size of the kernel may be arbitrarily determined, and the stride at which the kernel traverses input data may also be arbitrarily determined. A result of convolution of all input data per kernel may be referred to as a feature map or an activation map. Hereinafter, the kernel may include a set of weight values or a plurality of sets of weight values. The number of kernels for each layer may be referred to as the number of channels.

As such, since the convolution operation is an operation performed by convolving input data and a kernel, an activation function for adding non-linearity may be applied thereafter. When an activation function is applied to a feature map that is a result of a convolution operation, it may be referred to as an activation map.

Specifically, referring to FIG. 7, the convolutional neural network may include at least one convolutional layer, at least one pooling layer, and at least one fully connected layer. For example, convolution may be defined by two main parameters: the size of the input data (typically a 1×1, 3×3 or 5×5 matrix) and the depth of the output feature map (the number of kernels). These key parameters can be computed by convolution operation. These convolution operations may start at depth 32, continue to depth 64, and end at depth 128 or 256. The convolution operation may refer to an operation of sliding a kernel having a size of 3×3 or 5×5 over an input image matrix that is input data, multiplying each weight of the kernel and each element of the overlapping input image matrix, and then accumulating all of the multiplied values.

An activation function may be applied to the output feature map generated in this way to finally output an activation map. In addition, the weight used in the current layer may be transmitted to the next layer through convolution. The pooling layer may perform a pooling operation to reduce the size of the feature map by down sampling the output data (i.e., the activation map). For example, the pooling operation may include, but is not limited to, max pooling and/or average pooling.

The max pooling operation uses the kernel, and outputs the maximum value in the area of the feature map overlapping the kernel by sliding the feature map and the kernel. The average pooling operation outputs an average value within the area of the feature map overlapping the kernel by sliding the feature map and the kernel. As such, since the size of the feature map is reduced by the pooling operation, the number of weights of the feature map is also reduced.

The fully connected layer may classify data output through the pooling layer into a plurality of classes (i.e., inferenced result) and may output the classified class and a score thereof. Data output through the pooling layer may form a three-dimensional feature map, and this three-dimensional feature map can be converted into a one-dimensional vector and input as a fully connected layer.

Figure 8:
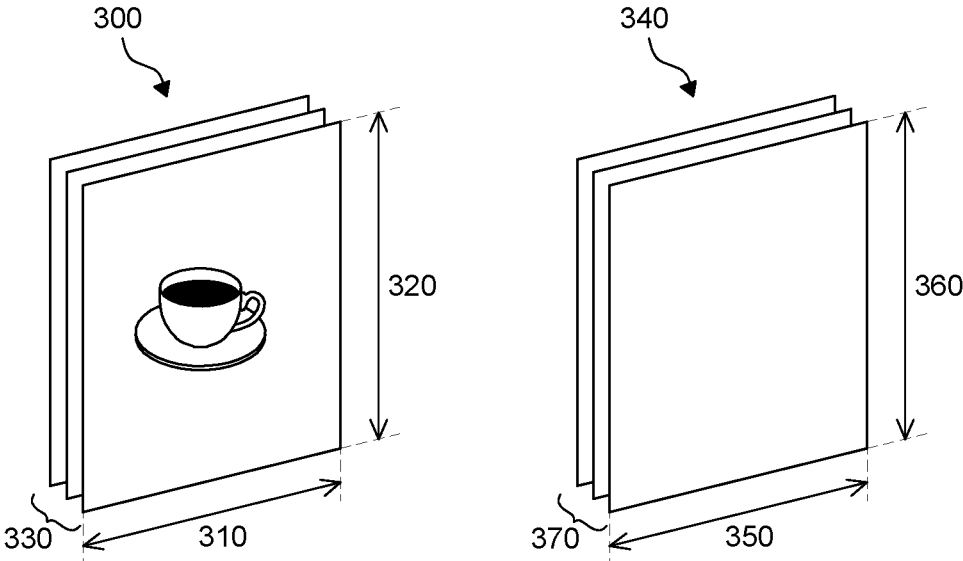
FIG. 8 is a diagram for explaining input data of the convolution layer shown in FIG. 7 and a kernel used for a convolution operation.

FIG. 8 shows input data of the convolution layer shown in FIG. 7 and a kernel used in a convolution operation.

Referring to FIG. 8, the input data 300 may be an image or an image displayed as a two-dimensional matrix composed of rows 310 of a specific size and columns 320 of a specific size. The input data 300 may be referred to as a feature map. The input data 300 may have a plurality of channels 330, where the channel 330 may represent a color RGB channel of the input data image.

Meanwhile, the kernel 340 may be a weight parameter used for convolution for extracting features of a certain portion of the input data 300 while scanning it. Like the input data image, the kernel 340 may be configured to have a specific size of rows 350, a specific size of columns 360, and a specific number of channels 370. In general, the size of the row 350 and the column 360 of the kernel 340 is set to be the same, and the number of channels 370 may be the same as the number of channels 330 of the input data image.

Figure 9:
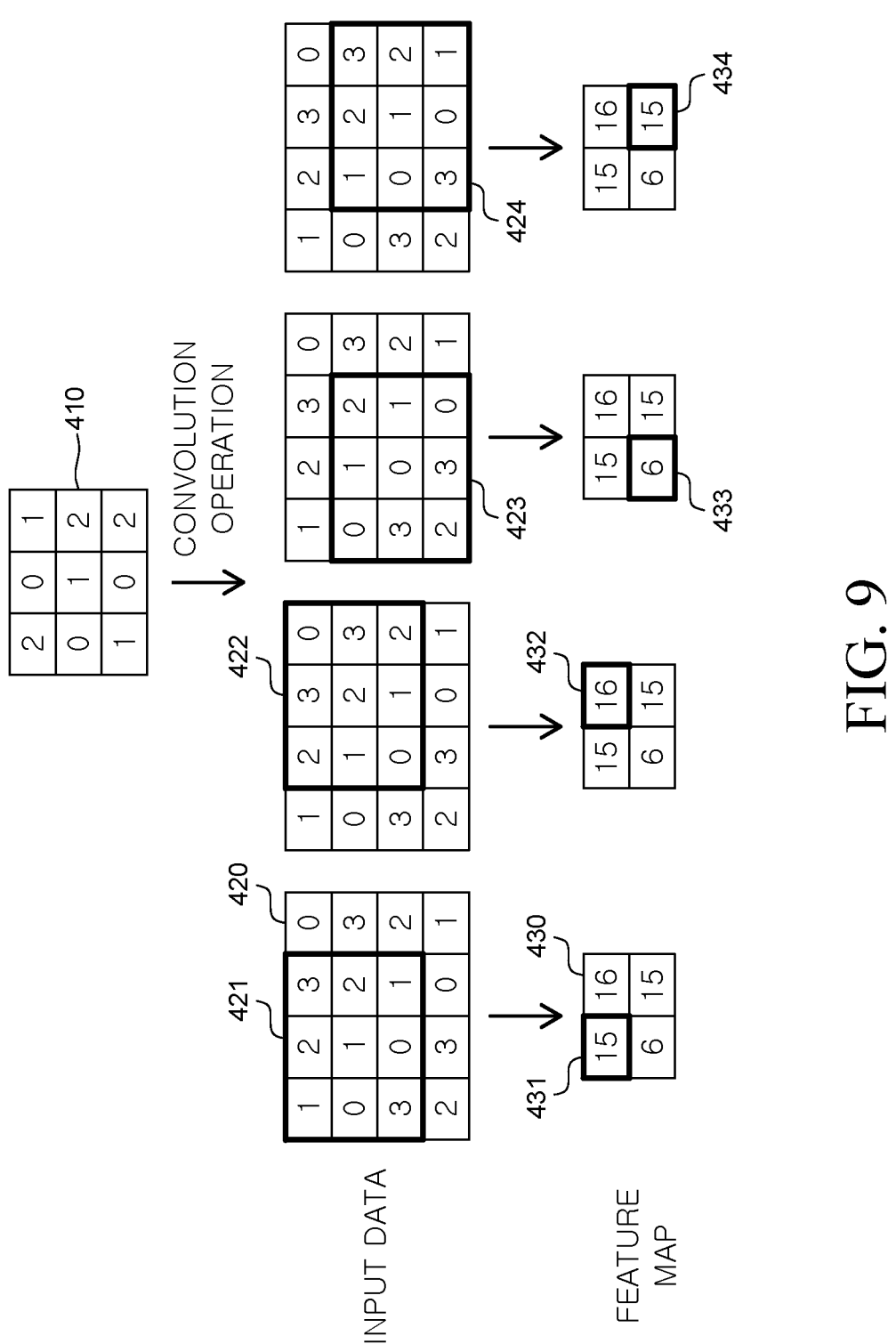
FIG. 9 is a diagram for explaining the operation of a convolutional neural network that generates a feature map using the kernel shown in FIG. 8.

FIG. 9 shows the operation of a convolutional neural network that generates a feature map using the kernel shown in FIG. 8.

Referring to FIG. 9, the kernel 410 may generate the feature map 430 by traversing the input data 420 at specified intervals and performing convolution. When the kernel 410 is applied to a portion of the input data 420, convolution may be performed by multiplying input data values at a specific position of a portion and values at the corresponding position in the kernel 410, and then summing all the generated values.

Through this convolution process, calculated values of the feature map are generated, and whenever the kernel 410 traverses the input data 420, the result values of the convolution are generated to configure the feature map 430.

Each element value of the feature map may be converted into the activation map 430 through the activation function of the convolution layer.

In FIG. 9, the input data 420 input to the convolution layer is represented by a two-dimensional matrix having a size of 4×4, and the kernel 410 is represented by a two-dimensional matrix having a size of 3×3. However, the sizes of the input data 420 and the kernel 410 of the convolution layer are not limited thereto, and may be variously changed according to the performance and requirements of the convolutional neural network including the convolution layer.

As shown, when the input data 420 is input to the convolution layer, the kernel 410 traverses the input data 420 at a predetermined interval (e.g., stride=1), the MAC operation of multiplying the values of the input data 420 and the kernel 410 at the same location and summing the respective values may be performed.

Specifically, the kernel 410 assigns the MAC operation value "15" calculated at a specific location 421 of the input data 420 to the corresponding element 431 of the feature map 430. The kernel 410 assigns the MAC operation value "16" calculated at the next position 422 of the input data 420 to the corresponding element 432 of the feature map 430. The kernel 410 assigns the MAC operation value "6" calculated at the next position 423 of the input data 420 to the corresponding element 433 of the feature map 430. Next, the kernel 410 assigns the MAC operation value "15" calculated at the next position 424 of the input data 420 to the corresponding element 434 of the feature map 430.

As described above, when the kernel 410 allocates all MAC operation values calculated while traversing the input data 420 to the feature map 430, the feature map 430 having a size of 2×2 can be generated.

At this time, if the input data 510 is composed of, for example, three channels (R channel, G channel, B channel), a feature map for each channel can be generated through convolution in which the same kernel or different channels for each channel are traversed over data for each channel of the input data 420 and multiply and accumulation operations are performed.

For the MAC operation, the NPU scheduler 130 may allocate the processing elements PE1 to PE12 to perform each MAC operation based on a predetermined operation sequence, and may set the memory address in which the MAC operation values are stored in the NPU internal memory 120 in consideration of the scheduling sequence.

Figure 10:
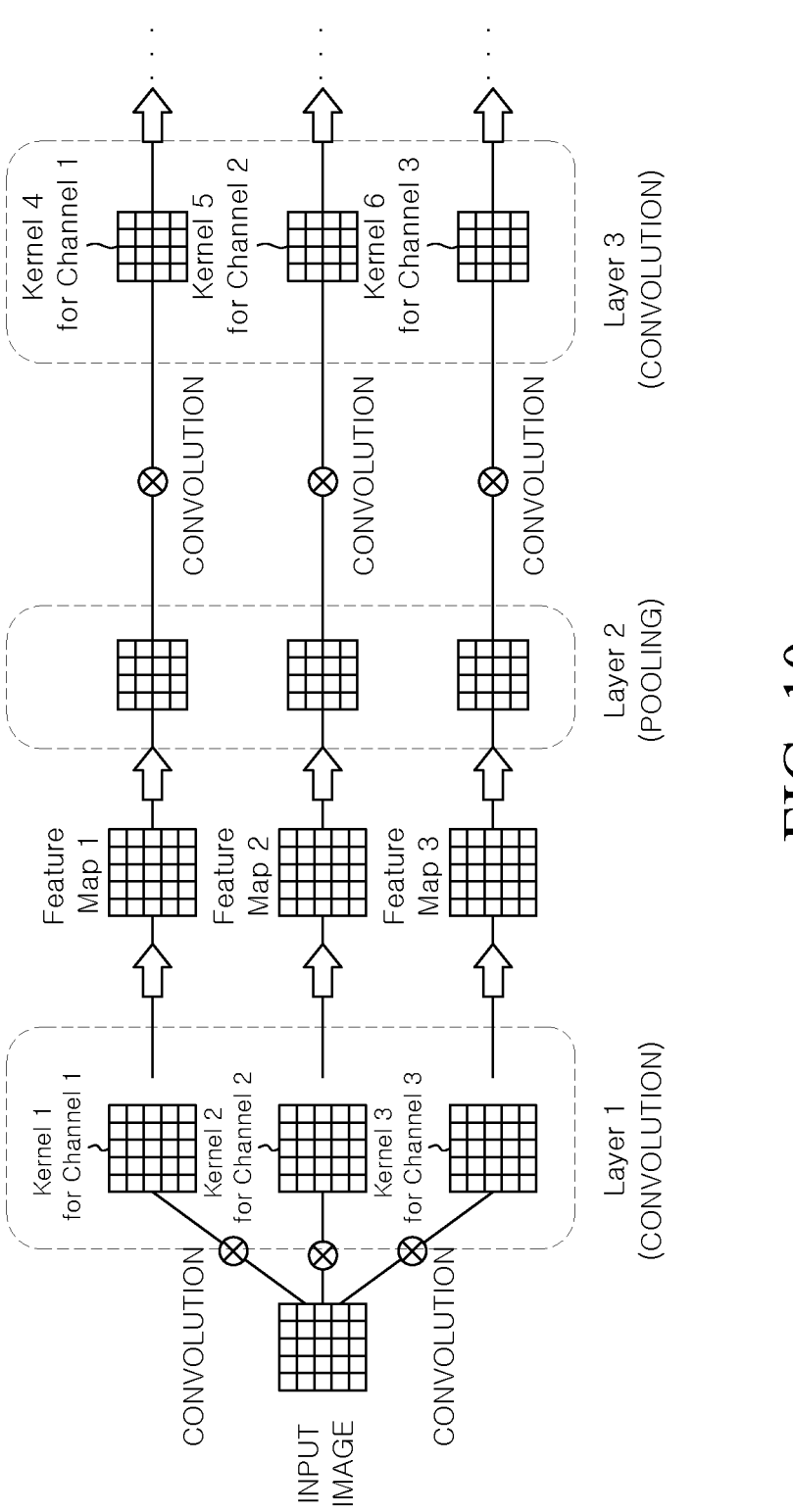
FIG. 10 is a comprehensive diagram illustrating the operation of the convolutional neural network shown in FIG. 7 for easy understanding.

FIG. 10 illustrates the operation of the convolutional neural network shown in FIG. 7 for easy understanding.

Referring to FIG. 10, for example, an input image is shown as a two-dimensional matrix having a size of 5×5. In addition, FIG. 10 shows three channels, i.e., channel 1, channel 2, and channel 3, are used as an example.

First, the convolution operation of layer 1 will be described.

The input image is convolved with kernel 1 for channel 1 at the first node of layer 1, and as a result, feature map 1 is output. Also, the input image is convolved with kernel 2 for channel 2 at the second node of layer 1, and as a result, feature map 2 is output. Also, the input image is convolved with kernel 3 for channel 3 at the third node, and as a result, feature map 3 is output.

Next, a layer 2 polling operation will be described.

The feature map 1, the feature map 2, and the feature map 3 output from the layer 1 are input to the three nodes of the layer 2. Layer 2 may receive feature maps output from layer 1 as input and then perform polling. The polling may reduce the size or emphasize a specific value in a matrix. Polling methods include maximum polling, average polling, and minimum value polling. Maximum polling is used to collect the maximum values of values within a specific region of a matrix, and average polling can be used to find the average within a specific region of a matrix.

In order to process each convolution, the processing elements PE1 to PE12 of the NPU 100 are configured to perform a MAC operation.

In the example of FIG. 10, the size of the feature map of a 5×5 matrix is reduced to a 4×4 matrix by polling.

Specifically, the first node of layer 2 receives the feature map 1 for channel 1 as an input, performs polling, and outputs it as, for example, a 4×4 matrix. The second node of layer 2 receives the feature map 2 for channel 2 as an input, performs polling, and outputs, for example, a 4×4 matrix. The third node of layer 2 receives the feature map 3 for channel 3 as an input, performs polling, and outputs, for example, a 4×4 matrix.

Next, the convolution operation of layer 3 will be described.

The first node of layer 3 receives the output from the first node of layer 2 as input, performs convolution with kernel 4, and outputs the result. The second node of layer 3 receives the output from the second node of layer 2 as input, performs convolution with kernel 5 for channel 2, and outputs the result. Similarly, the third node of layer 3 receives the output from the third node of layer 2 as input, performs convolution with kernel 6 for channel 3, and outputs the result.

In this way, convolution and polling are repeated, and finally, as shown in FIG. 9, it may be input to a fully connected layer.

Meanwhile, in order to perform more in-depth prediction of cardiovascular disease in the user device 10, the need for a fusion algorithm for processing a variety of different sensing data related to the user is emerging. Hereinafter, fusion algorithms are introduced through FIGS. 11 to 13.

Figure 11:
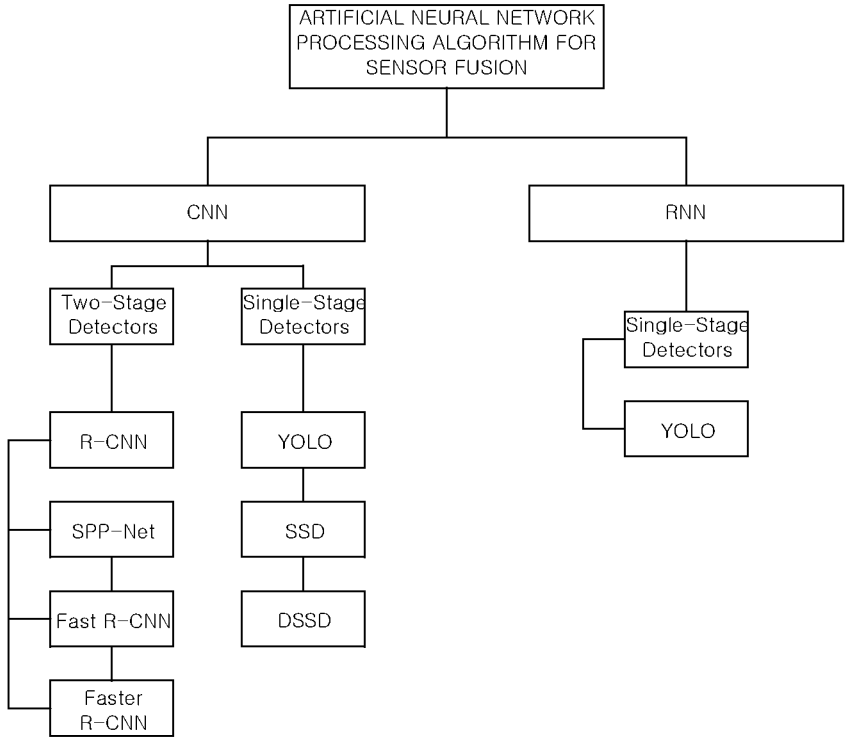
FIG. 11 is a conceptual diagram illustrating an example of an algorithm applicable to an artificial neural network model for predicting cardiovascular disease according to an example of the present disclosure.

FIG. 11 illustrates an example of an algorithm applicable to an artificial neural network model for predicting disease according to an example of the present disclosure.

Referring to FIG. 11, a convolutional neural network (CNN) and a recurrent neural network (RNN) may be exemplarily used to process different data provided from heterogeneous sensors. A CNN can be used to detect an object in one image, and an RNN can be used to predict an object using the time domain. In addition, region-based CNN (R-CCN), spatial pyramid pooling network (SPP-Net), you only look once (YOLO), single-shot multi-box detector (SSD), deconvolutional single-shot Multi-box detector (DSSD), long-short term memory (LTSM), gated recurrent unit (GRU), and the like may be used.

Figure 12:
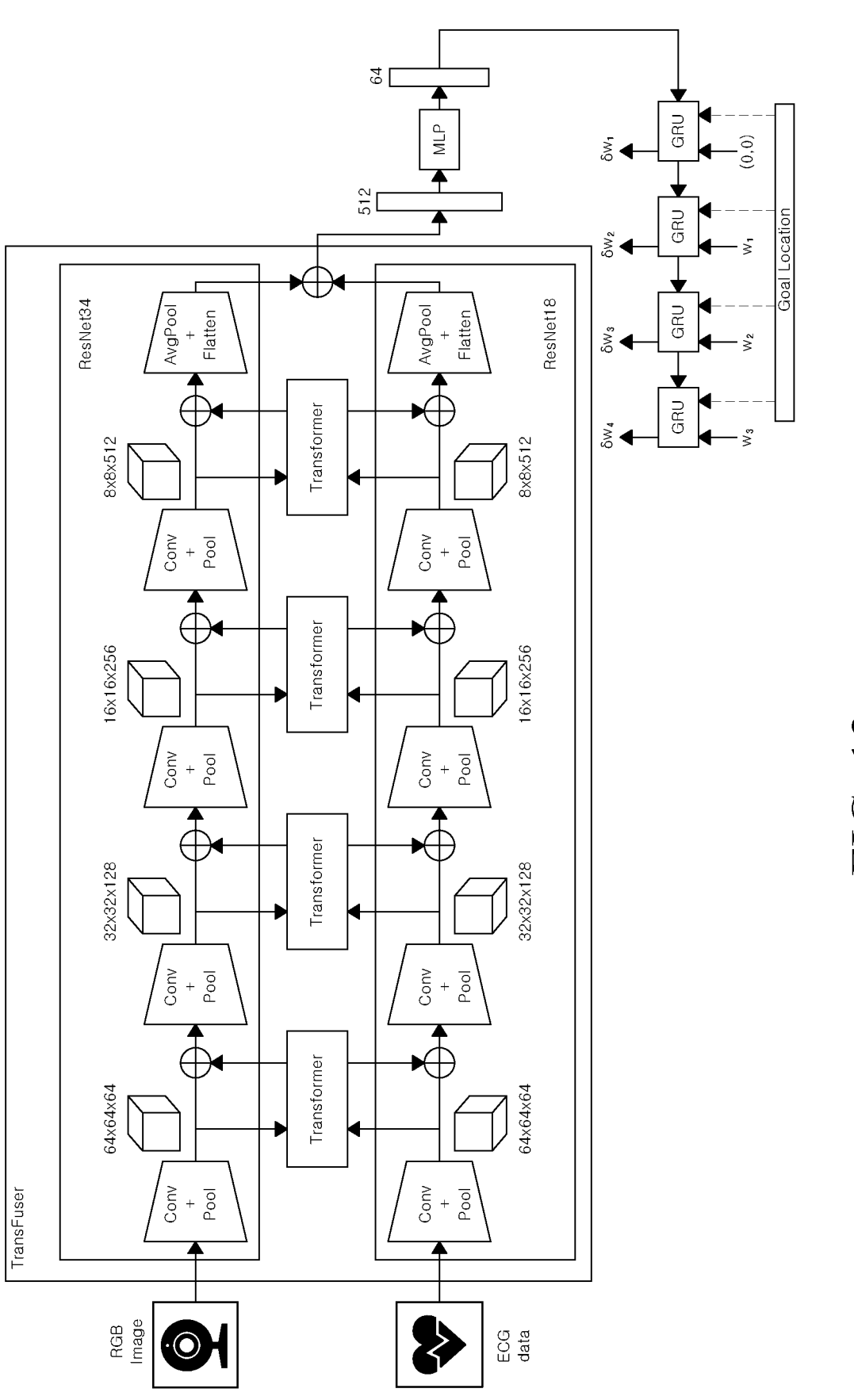
FIG. 12 is a conceptual diagram illustrating an artificial neural network model for predicting cardiovascular disease according to an example of the present disclosure.

FIG. 12 illustrates an artificial neural network model for predicting cardiovascular disease according to an example of the present disclosure.

Referring to FIG. 12, an example of processing signals provided from a camera and an ECG sensor through parallel processing is illustrated. During parallel processing, different information can be exchanged through transformers. The method may be a deep fusion method shown in FIG. 13 to be described later.

Meanwhile, although not shown, the artificial neural network may include a concatenation operation and a skip-connection operation in order to process different data provided from heterogeneous sensors. The concatenation operation means to combine the output results of a specific layer with each other, and the skip-connection operation means to pass the output result of a specific layer to another layer while skipping subsequent layers.

Such a concatenation operation and a skip-connection operation may increase control difficulty and usage of the internal memory 120 of the NPU 100.

So far, artificial neural networks for fusion and processing of different data provided from heterogeneous sensors have been described, but there is a weakness that cannot improve the performance of artificial neural networks only with the above description. Accordingly, the optimized artificial neural network and NPU structure will be described below.

Fusion Artificial Neural Network and NPU Structure Optimized to Process Different Data from Heterogeneous Sensors First, the inventor of the present disclosure has studied NPUs for processing different data from heterogeneous sensors.

In the design of the NPU, the following configuration should be considered:

I. It is necessary to have an NPU structure suitable for heterogeneous data signal processing (e.g., camera+ ECG sensor).

II. NPU memory control suitable for heterogeneous input signal processing (e.g., RGB camera+ECG sensor) is required.

III. It is necessary to have an NPU structure suitable for multiple input channels.

IV. NPU memory control suitable for multiple input channels is required.

V. It is necessary to have an NPU structure suitable for computing a cardiovascular disease prediction artificial neural network model (fusion artificial neural network model).

VI. Fast processing speed of less than 16 ms is required for real-time application.

VII. It is necessary to achieve low power consumption for battery operation.

An NPU for implementing a cardiovascular disease prediction artificial neural network model (fusion artificial neural network model) should support the following functions. Expected requirements may include:

I. CNN function support: It should be able to control PE array and memory optimized for convolution.

II. It should be able to efficiently handle depthwise-separable convolutions. It should have a structure that improves PE utilization rate and performance.

III. Batch mode function support: Memory configuration is required to process multiple channels (e.g., cameras 1 to 6) and heterogeneous sensors at the same time (e.g., PE array size and memory size must be in an appropriate ratio).

IV. Concatenation function support: An NPU for cardiovascular disease prediction artificial neural network model (fusion artificial neural network model) should be able to process heterogeneous input data signals with concatenation function.

V. Support for skip connection function: NPU for cardiovascular disease prediction artificial neural network model (fusion artificial neural network model) may include a special function unit (SFU) that can provide skip-connection function.

VI. Support for deep learning image pre-processing function: An NPU for cardiovascular disease prediction artificial neural network model (fusion artificial neural network model) should be able to provide the function of pre-processing different data signals.

VII. A compiler capable of efficiently compiling a cardiovascular disease prediction artificial neural network model (fusion artificial neural network model) should be provided.

The inventor of the present disclosure proposes an NPU having the following characteristics.

I. The NPU may include a compiler that analyzes ANN data locality information of a cardiovascular disease prediction artificial neural network, such as late fusion, early fusion, and deep fusion.

II. The NPU may be configured to control the processing element array to process heterogeneous sensor data based on an artificial neural network data locality controller (ADC). That is, the cardiovascular disease prediction artificial neural network is fused into various structures depending on the sensor, and the PE utilization rate can be improved by providing the NPU 100 corresponding to the structure.

III It may be configured to appropriately set the size of the on-chip internal memory 120 to process heterogeneous sensor data based on the ANN data locality information. That is, the memory bandwidth of the NPU 100 processing the fusion artificial neural network can be improved by analyzing the artificial neural network data locality information of the cardiovascular disease prediction artificial neural network model (fusion artificial neural network model).

IV. The NPU may include a special function unit (SFU) that can efficiently process bilinear interpolation, concatenation, skip-connection and the like required in a fusion artificial neural network.

Figure 13:
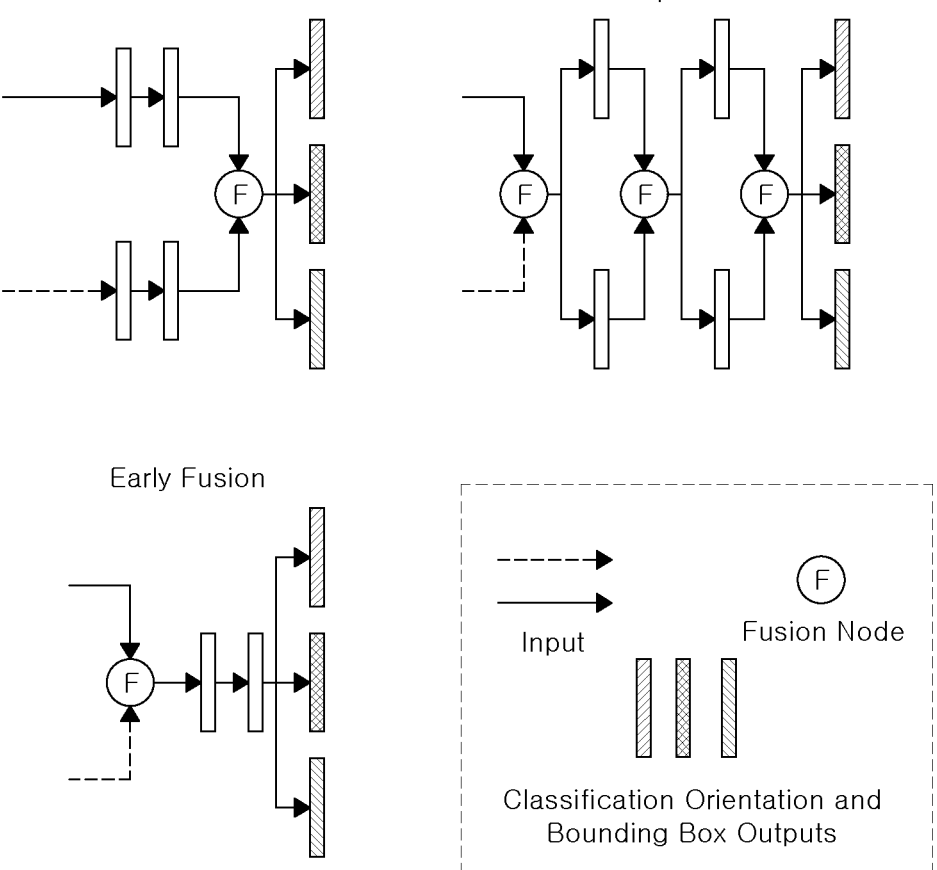
FIG. 13 is an exemplary diagram illustrating a fusion method of an NPU according to an example of the present disclosure.

FIG. 13 illustrates a fusion method of an NPU according to an example of the present disclosure.

Referring to FIG. 13, "F" indicates a fusion operation, and each block indicates each layer. As can be seen with reference to FIG. 13, late fusion may be referred to as performing an operation for each layer and then fusion of the operation result in the final process. Early fusion may be referred to as early fusion of different data and then performing an operation for each layer. Deep fusion may be referred to as fusion of heterogeneous data, performing an operation in different layers, fusion of the operation results again, and then performing an operation for each layer.

Hereinafter, the structure of the NPU 100 capable of disclosing the above features will be described.

Figure 14:
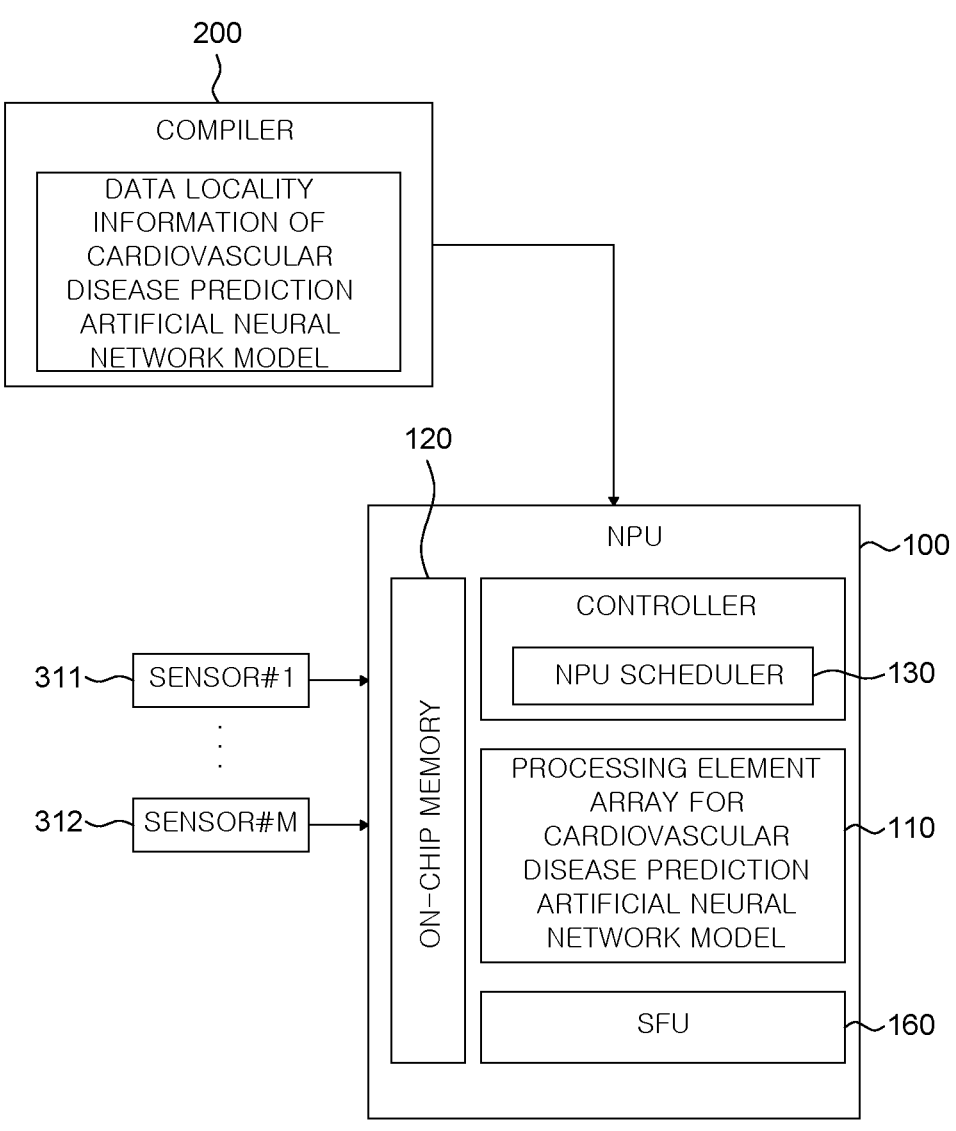
FIG. 14 is a conceptual diagram illustrating a system including an NPU architecture according to a first example of the present disclosure.

FIG. 14 illustrates a system including the NPU architecture according to the first example.

Referring to FIG. 14, the NPU 100 may include a processing element array 110 for a cardiovascular disease prediction artificial neural network model, an on-chip memory 120, an NPU scheduler 130, and a special function unit (SFU) 160. For describing FIG. 14, redundant descriptions may be omitted for convenience of description only.

The processing element array 110 for the cardiovascular disease prediction artificial neural network may refer to the array of processing element 110 configured to process the convolution of a multi-layered cardiovascular disease prediction neural network model having at least one fusion layer. That is, the fusion layer may be configured to output a feature map in which data of heterogeneous sensors are fused. In more detail, the SFU 160 of the NPU 100 may be configured to receive multiple sensors and provide a function of fusion of each sensor input. The processing element array 110 for the cardiovascular disease prediction artificial neural network may be configured to receive fusion data from the SFU 160 and process convolution.

The NPU 100 may receive heterogeneous data from the M heterogeneous sensors 311 and 312. The heterogeneous sensors may include a microphone, a touch screen, a camera, an altimeter, a barometer, an optical blood flow sensor, an electrocardiogram sensor, an inertial sensor, a geo-positioning system, an optical sensor, a thermometer, an electromyography sensor, and the like.

The NPU 100 may obtain cardiovascular disease prediction artificial neural network (fusion ANN) data locality information from the compiler 200.

At least one layer of the cardiovascular disease prediction artificial neural network may be a layer in which input data of a plurality of sensors are fused.

The NPU 100 may be configured to provide a concatenation function to at least one layer for fusion of heterogeneous sensor input data. In order to connect each feature map of the heterogeneous sensors of the concatenated layer to each other, the size of at least one axis may be processed to be the same. For example, in order to concatenate heterogeneous sensor data along the x-axis, the size of the x-axis of each of the different types of sensor data may be the same. For example, in order to concatenate heterogeneous sensor data along the y-axis, the y-axis size of each of the heterogeneous sensor data may be the same. For example, in order to concatenate heterogeneous sensor data along the z-axis, the z-axis sizes of the different types of sensor data may be the same. In order to improve the processing efficiency of the NPU 100, the size of one of the heterogeneous sensor data may be scaled up or scaled down. Accordingly, it is also possible that the sizes of one axis of the fused data of heterogeneous sensor data are the same. In other words, since the processing element array 100 is in the form of an N×M matrix, the PE utilization rate of the processing element array 100 may vary according to the size of at least one axis of sensor data.

In order to receive and process heterogeneous data from the heterogeneous sensors 311 and 312, the NPU scheduler 130 may process inference of a cardiovascular disease prediction artificial neural network model (fusion artificial neural network model).

The NPU scheduler 130 may be included in the controller as illustrated.

The NPU scheduler 130 may obtain and analyze data locality information of a cardiovascular disease prediction artificial neural network model (fusion artificial neural network model) from the compiler 200, and may control the operation of the on-chip memory 120.

Specifically, the compiler 200 may generate data locality information of a fusion artificial neural network to be processed by the NPU 100.

The NPU scheduler 130 may generate a list for a special function operation required for the cardiovascular disease prediction artificial neural network model (fusion artificial neural network model). The special function may mean various functions required for artificial neural network operation other than convolution operation.

If the cardiovascular disease prediction artificial neural network model (fusion artificial neural network model) data locality information is efficiently utilized, it is possible to efficiently decrease the frequency of increasing memory access problem, which frequently occurs in fusion artificial neural networks, such as non-maximum suppression (NMS), skip-connection, bottleneck, and bilinear interpolation and the like.

If cardiovascular disease prediction artificial neural network model (fusion artificial neural network model) data locality information is utilized, the size of the data (i.e., the first feature map) to be stored and a period of the data to be stored can be analyzed in the compilation stage with respect to the fusion of the first output feature map information to be processed first and the second output feature map information to be processed next. Accordingly, a memory map for the on-chip memory 120 can be efficiently set in advance.

The SFU 160 may perform skip-connection and concatenation necessary for a cardiovascular disease prediction artificial neural network model (fusion artificial neural network model). In other words, concatenation can be utilized to fuse heterogeneous sensor data. For concatenation, the size of each sensor data can be readjusted. For example, the NPU 100 may be configured to handle the concatenation of the fused artificial neural network by providing functions such as resizing, interpolation, and the like.

The on-chip memory 120 of the NPU 100 may selectively preserve specific data according to the processing element array 110 or the SFU 160 for a specific period based on the cardiovascular disease prediction artificial neural network data locality information. Whether or not to preserve the selective storage may be controlled by the controller.

Also, the processing element array 110 may be configured to have a plurality of threads corresponding to the number of heterogeneous sensors. That is, the array 110 of the NPU 100 configured to receive two sensor data may be configured to have two threads. That is, if a thread is configured with N×M processing elements, two threads may be configured with N×M×2 processing elements. For example, each thread of the processing element array 110 may be configured to process a feature map of each heterogeneous sensor.

The NPU 100 may output the operation result of the cardiovascular disease prediction artificial neural network through an output unit.

The NPU architecture according to the first example described above may be variously modified.

Figure 15A:
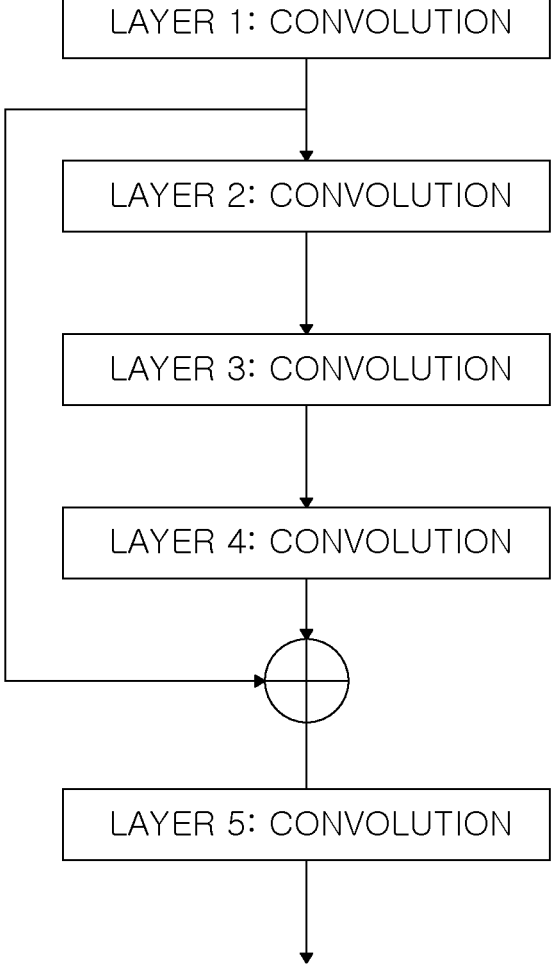
FIG. 15A is an exemplary diagram for explaining skip-connection included in an artificial neural network model for predicting cardiovascular disease according to the first example of the present disclosure.

FIG. 15A illustrates a model of a cardiovascular disease prediction artificial neural network including skip-connection. FIG. 15B illustrates locality information of artificial neural network data of the artificial neural network model for predicting cardiovascular disease shown in FIG. 15A.

Referring to FIG. 15A, in order to calculate five layers including a skip-connection operation, for example, as shown in FIG. 15B, the compiler 200 may generate cardiovascular disease prediction artificial neural network data locality information having a sequence of sixteen stages.

The NPU 100 may request a data operation to the on-chip memory 120 according to the sequence of the cardiovascular disease prediction artificial neural network data locality information.

In the case of a skip-connection operation, the output feature map OFMAP of the first layer may be added to the output feature map OFMAP of the fourth layer.

For such a skip-connection operation, the output feature map of the first layer must be preserved until the fifth layer operation. However, other data may be deleted after operation in order to utilize memory space.

In the deleted memory area, data to be calculated later based on the sequence of artificial neural network data locality information may be stored. Accordingly, it is possible to sequentially bring necessary data to the on-chip memory 120 according to the sequence of the cardiovascular disease prediction artificial neural network data area information, and delete data that is not reused. Accordingly, even if the memory size of the on-chip memory 120 is small, the operating efficiency of the on-chip memory 120 may be improved.

Therefore, the NPU 100 may selectively preserve or delete specific data of the on-chip memory 120 for a predetermined period based on the cardiovascular disease prediction artificial neural network data locality information.

Such a principle may be applied not only to a skip-connection operation, but also to various operations such as concatenation, non-maximum suppression (NMS), and bilinear interpolation.

For example, the NPU 100 performs the convolution operation of the second layer for efficient control of the on-chip memory 120 and then deletes the data of the first layer except for the output feature map OFMAP of the first layer. As another example, after performing the operation of the third layer for efficient control of the on-chip memory 120, the NPU 100 may delete data of the second layer except for the output feature map OFMAP of the first layer. As another example, after the NPU 100 performs the operation of the fourth layer for efficient control of the chip-internal memory 120, the data of the third layer except for the output feature map OFMAP of the first layer may be deleted. Further, after the NPU 100 performs the operation of the fifth layer for efficient control of the chip-internal memory 120, the data of the fourth layer and the output feature map OFMAP of the first layer may be deleted.

The cardiovascular disease prediction artificial neural network data locality information may include a data processing sequence to be generated by the compiler 200 and performed by the NPU 100 in consideration of the conditions listed below.

1. Structure of ANN model (fusion artificial neural networks such as Resnet, YOLO, SSD, and the like designed to receive heterogeneous sensor data).
2. Processor architecture (e.g., CPU, GPU, NPU, etc. architecture). In the case of NPU, the number of processing elements, the structure of the processing element (e.g., input stationary structure, output stationary structure, weight stationary structure, and the like), SFU structure configured to operate with the array of processing element, and the like.
3. On-chip memory 120 size (e.g., a tiling algorithm to be required when the cache size is smaller than the data, and the like).

4. Data size of each layer of the cardiovascular disease prediction artificial neural network model to be processed.
5. Processing Policy, that is, the NPU 100 determines the sequence of whether the input feature map (IFMAP) read is requested first or the kernel read is request first. This may vary depending on the processor 12 or compiler 200.

Figure 16:
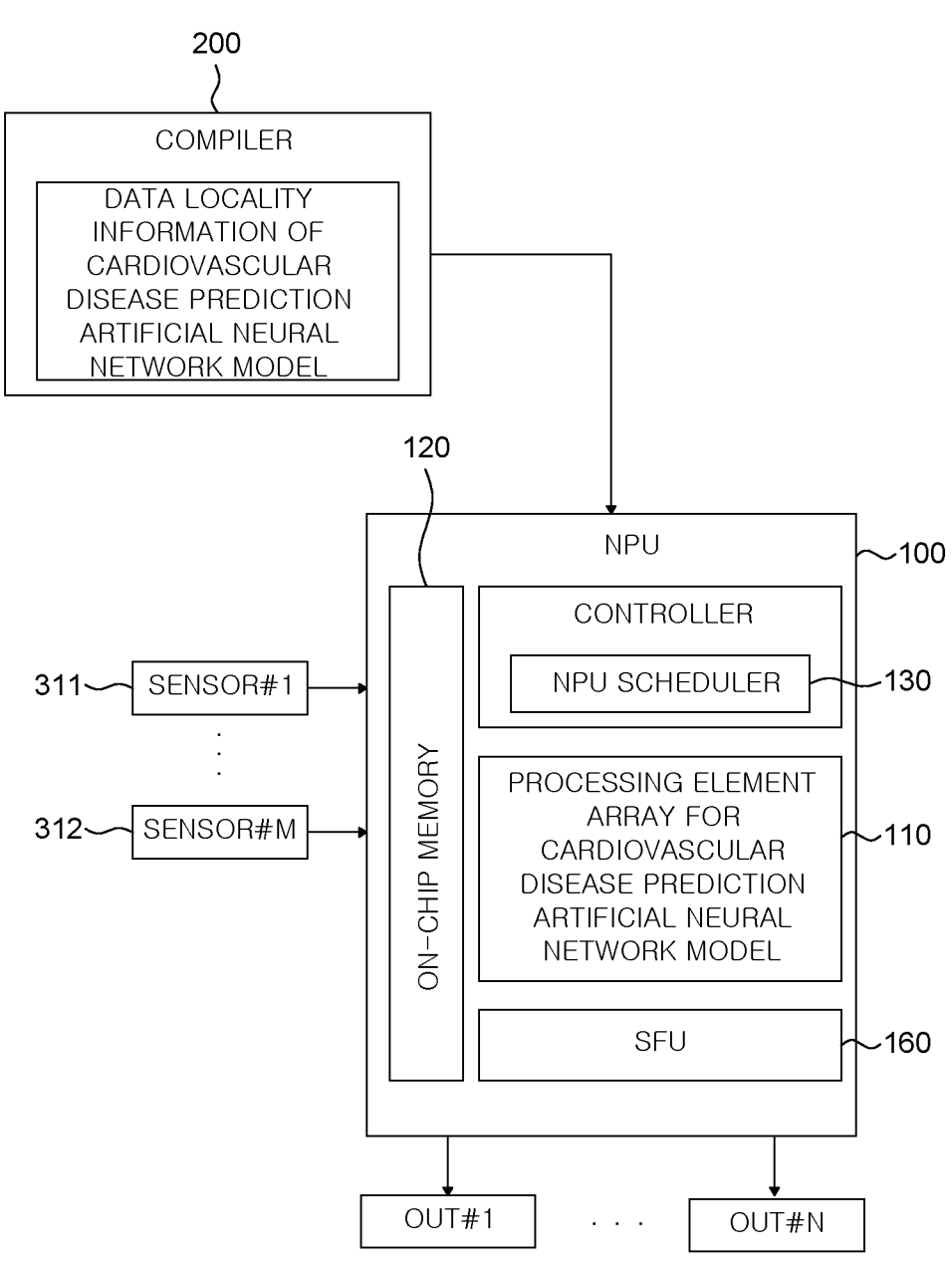
FIG. 16 is a conceptual diagram illustrating a system including an NPU architecture according to a second example of the present disclosure.

FIG. 16 illustrates a system including an NPU architecture according to a second example of the present disclosure.

Referring to FIG. 16, the NPU 100 may include a processing element array 110 for a fusion artificial neural network, an on-chip memory 120, an NPU scheduler 130, and a special function unit (SFU) 160. For describing FIG. 16, redundant descriptions may be omitted for convenience of description only.

The NPU scheduler 130 may be included in the controller as illustrated.

The NPU 100 may receive heterogeneous data from the M heterogeneous sensors 311 and 312. The heterogeneous sensors may include a microphone, a touch screen, a camera, an altimeter, a barometer, an optical blood flow sensor, an electrocardiogram sensor, an inertial sensor, a geo-positioning system, an optical sensor, a thermometer, an electromyography sensor, and the like.

The NPU 100 may obtain cardiovascular disease prediction artificial neural network data locality information from the compiler 200.

The NPU 100 may output N results (e.g., heterogeneous inference results) through N output units. The heterogeneous data output from the NPU 100 may be classification, semantic segmentation, object detection, prediction, or the like.

Figure 17:
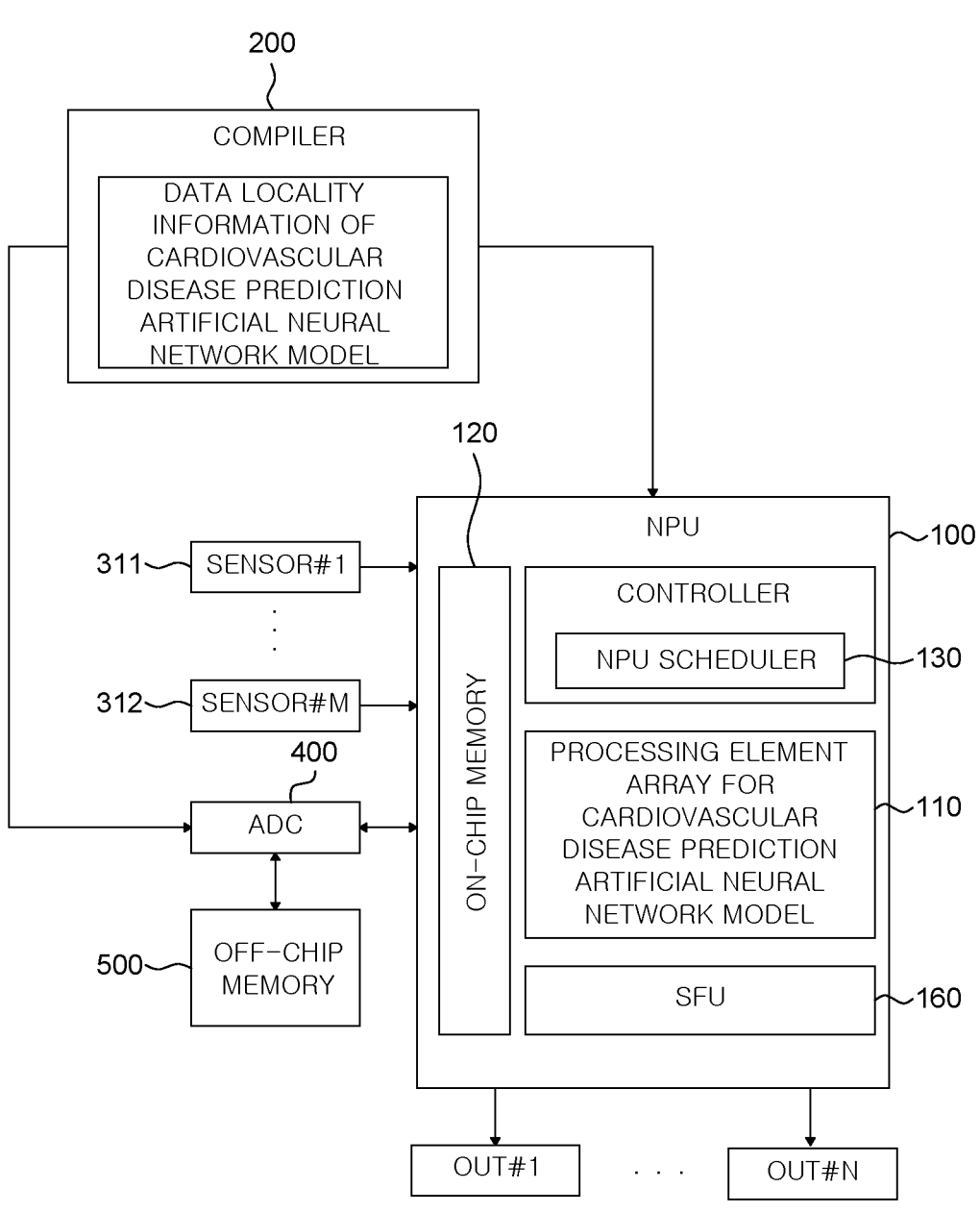
FIG. 17 is a conceptual diagram illustrating a system including an NPU architecture according to a third example of the present disclosure.

FIG. 17 illustrates a system including an NPU architecture according to a third example.

Referring to FIG. 17, the NPU 100 may include a processing element array 110 for a fusion artificial neural network, an on-chip memory 120, an NPU scheduler 130, and a special function unit (SFU) 160. For describing FIG. 17, redundant descriptions may be omitted for convenience of description only.

The NPU scheduler 130 may be included in the controller as illustrated.

The NPU 100 may receive heterogeneous data from the M heterogeneous sensors 311 and 312. The heterogeneous sensors may include a microphone, a touch screen, a camera, an altimeter, a barometer, an optical blood flow sensor, an electrocardiogram sensor, an inertial sensor, a geo-positioning system, an optical sensor, a thermometer, an electromyography sensor, and the like.

The NPU 100 may obtain cardiovascular disease prediction artificial neural network data locality information from the compiler 200.

The NPU 100 may receive data necessary for cardiovascular disease prediction artificial neural network operation from the off-chip memory 500 through an artificial neural network data locality controller (ADC) 400.

The ADC 400 may manage data in advance based on cardiovascular disease prediction artificial neural network data locality information of an artificial neural network model predicting cardiovascular disease provided from the compiler 200.

Specifically, the ADC 400 may receive and analyze artificial neural network data locality information of a cardiovascular disease prediction artificial neural network from the compiler 200 or by receiving the analyzed information from the compiler to control the operation of the off-chip memory 500.

The ADC 400 may read data stored in the off-chip memory 500 and cache the data stored in the off-chip memory 500 in advance in the on-chip memory according to the cardiovascular disease prediction neural network data locality information. The off-chip memory 500 may store all weight kernels of the cardiovascular disease prediction artificial neural network. In addition, the off-chip memory 120 may store only at least a portion of the weight kernels necessary according to the cardiovascular disease prediction artificial neural network data locality information among all the weight kernels stored in the off-chip memory 500. The memory capacity of the off-chip memory 500 may be greater than the memory capacity of the on-chip memory 120.

The ADC 400 may be configured to prepare data, required for the NPU 100 independently or interlocked with the NPU 100 based on the cardiovascular disease prediction artificial neural network data locality information, in advance from the off-chip memory 500 to reduce the latency of the inference operation of the NPU 100 or to improve the operation speed.

The NPU 100 may output N results (e.g., heterogeneous inference results) through N output units.

Figure 18:
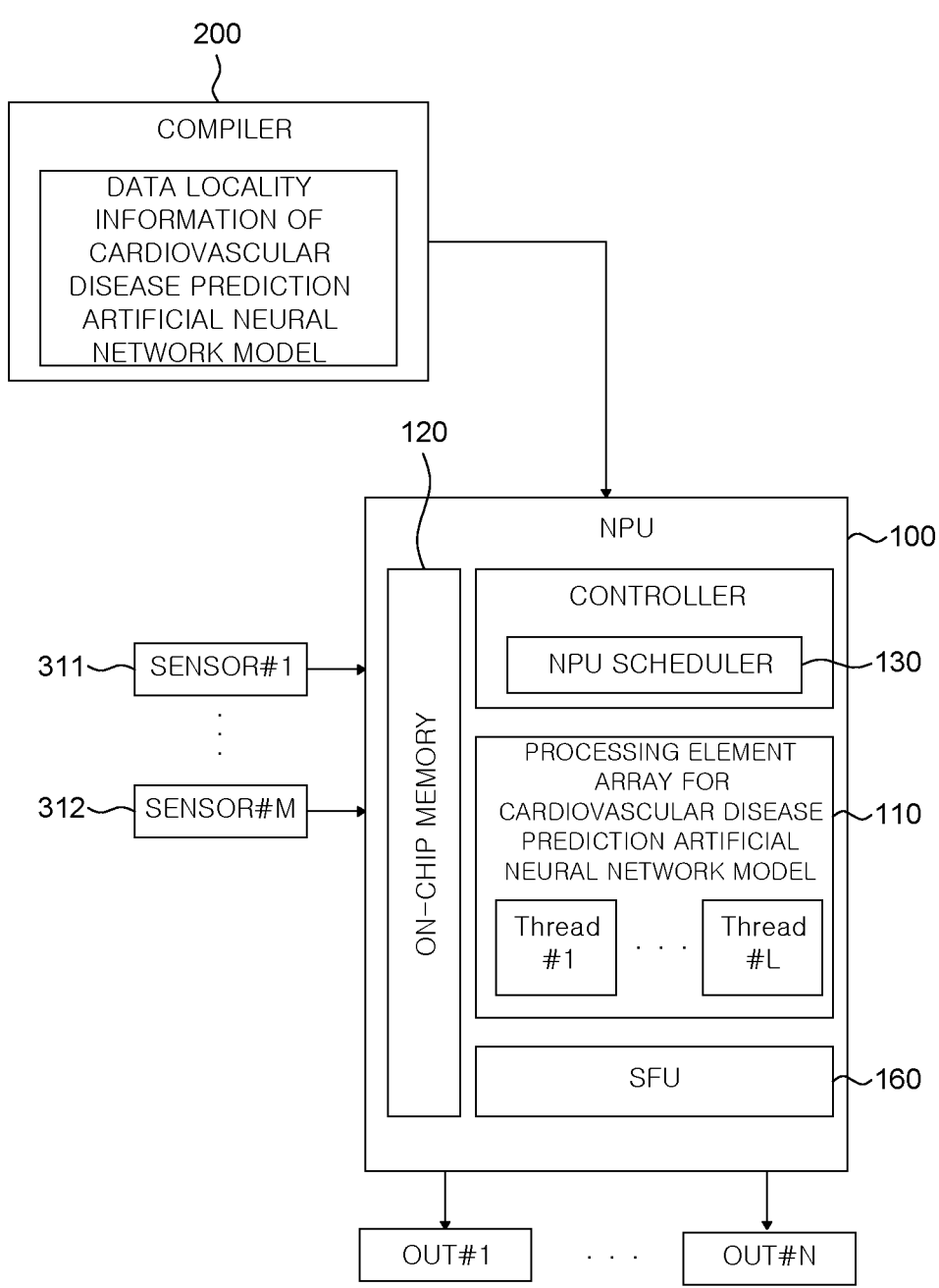
FIG. 18 is a conceptual diagram illustrating a system including an NPU architecture according to a fourth example of the present disclosure.
Figure 19:
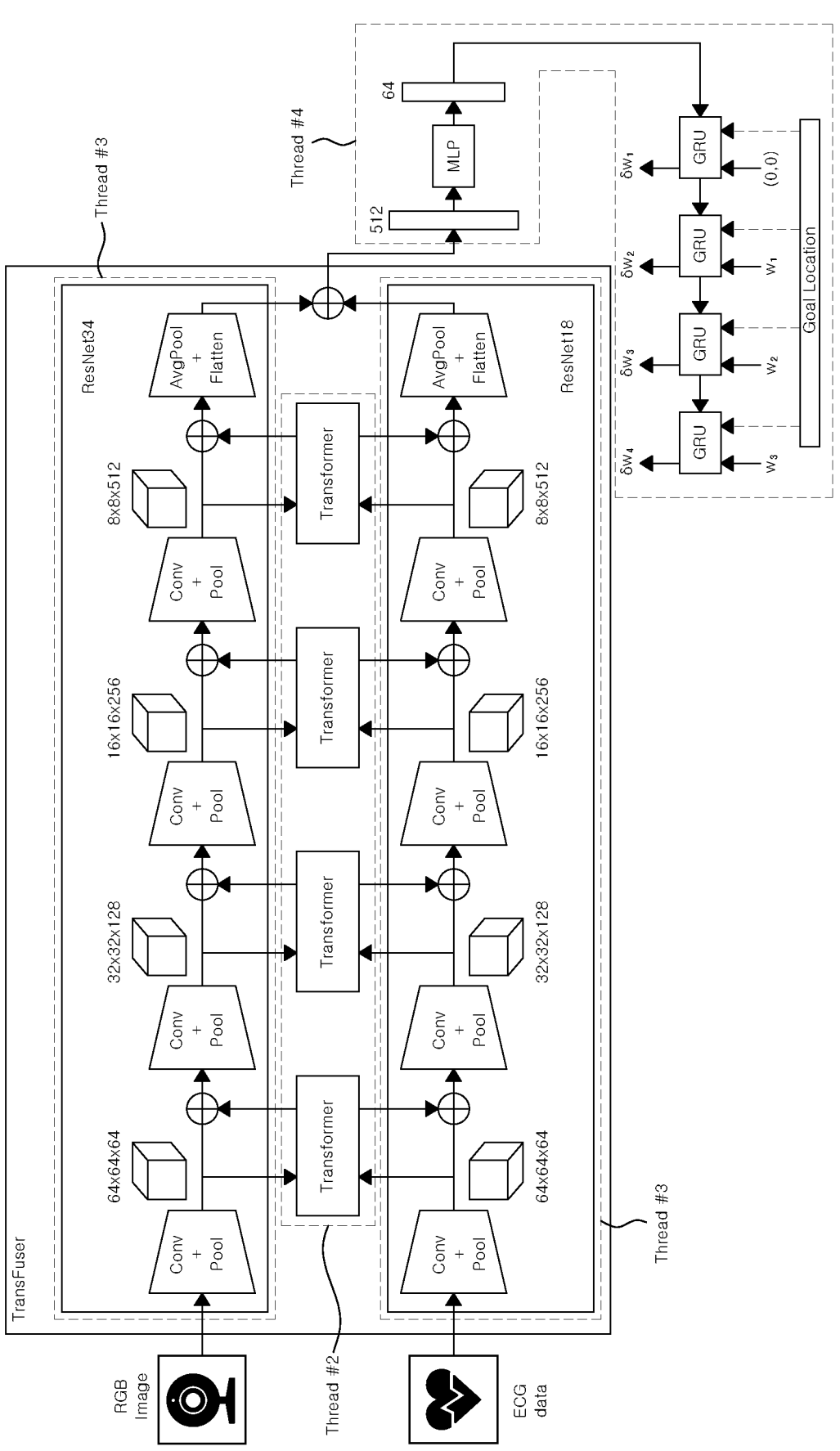
FIG. 19 is an exemplary diagram illustrating an example in which the artificial neural network model for predicting cardiovascular disease shown in FIG. 12 is divided into threads according to the fourth example shown in FIG. 18.

FIG. 18 illustrates a system including an NPU architecture according to a fourth example. FIG. 19 illustrates an example in which the fusion artificial neural network shown in FIG. 12 is divided into threads according to the fourth example shown in FIG. 18.

Referring to FIG. 18, the NPU 100 may include a processing element array 110 for a cardiovascular disease prediction artificial neural network model, an on-chip memory 120, an NPU scheduler 130, and a special function unit (SFU) 160.

The NPU scheduler 130 may be included in the controller as illustrated.

The NPU 100 may receive heterogeneous data from the M heterogeneous sensors 311 and 312. The heterogeneous sensors may include a microphone, a touch screen, a camera, an altimeter, a barometer, an optical blood flow sensor, an electrocardiogram sensor, an inertial sensor, a geo-positioning system, an optical sensor, a thermometer, an electro-myography sensor, and the like.

The NPU 100 may obtain cardiovascular disease prediction artificial neural network data locality information from the compiler 200.

The NPU 100 may output N results (e.g., heterogeneous inference results) through N output units. The heterogeneous data output from the NPU 100 may be classification, semantic segmentation, object detection, prediction, or the like.

The processing element array 110 can be processed as multiple threads. As shown in FIG. 19, RGB image data obtained from the camera may be processed through thread #1, conversion may be processed through thread #2, and data obtained from the ECG sensor may be processed through thread #3.

To this end, the compiler 200 may analyze the cardiovascular disease prediction artificial neural network model and classify the threads based on the parallel operation flow. The processing element array 110 of the NPU 100 can improve computational efficiency through multiple threads for a layer capable of parallel processing of a cardiovascular disease prediction artificial neural network.

The processing element array 110 of the NPU 100 may include a pre-determined thread.

The NPU 100 may control each thread of the processing element array 110 to communicate with the on-chip memory 120.

The NPU 100 may selectively allocate an internal space of the on-chip memory 120 for each thread.

The NPU 100 may allocate an appropriate space of the on-chip memory 120 for each thread. The memory allocation of the on-chip memory 120 may be determined by the controller based on artificial neural network data locality information of the cardiovascular disease prediction artificial neural network model.

The NPU 100 may set a thread in the processing element array 110 based on a fusion artificial neural network.

The NPU 100 may output N results (e.g., heterogeneous inference results) through N output units.

Figure 20:
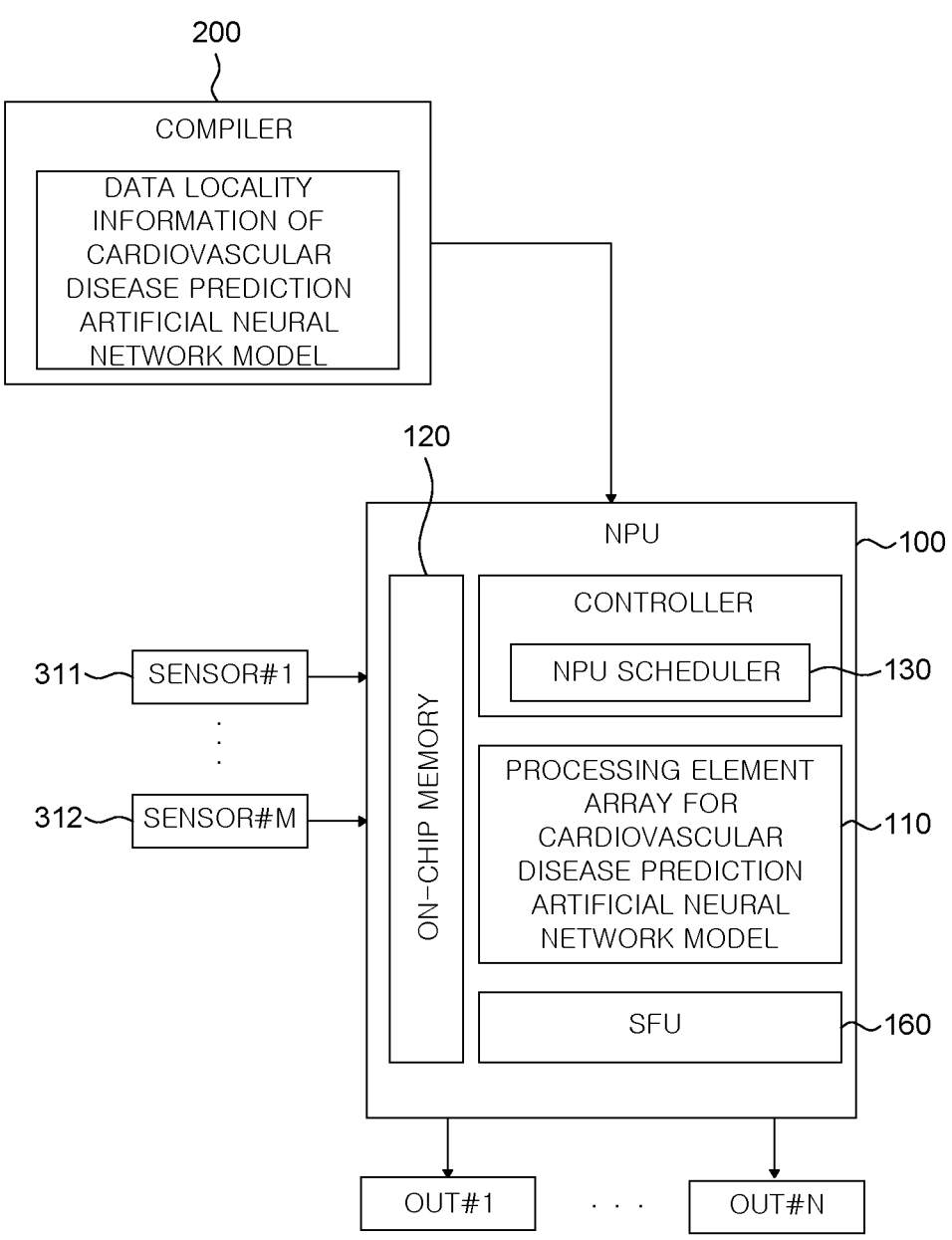
FIG. 20 is a conceptual diagram illustrating a system including an NPU architecture according to a fifth example of the present disclosure.
Figure 21:
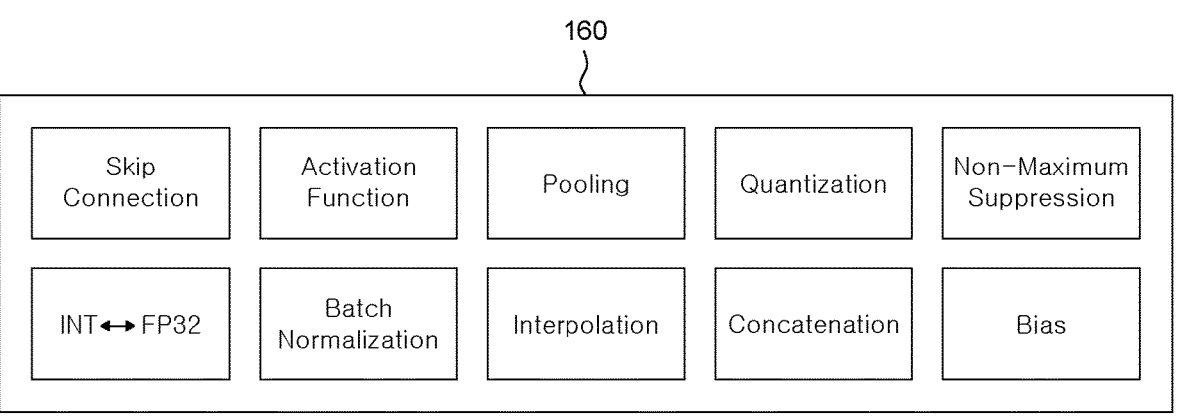
FIG. 21 is an exemplary view showing a first example of a pipeline structure of the SFU shown in FIG. 20.

FIG. 20 illustrates a system including an NPU architecture according to a fifth example. FIG. 21 illustrates a first example of the pipeline structure of the SFU shown in FIG. 20.

Referring to FIG. 20, the NPU 100 may include a processing element array 110 for a cardiovascular disease prediction artificial neural network model, an on-chip memory 120, an NPU scheduler 130, and a special function unit (SFU) 160.

The NPU 100 may receive heterogeneous data from the M heterogeneous sensors 311 and 312. The heterogeneous sensors may include a microphone, a touch screen, a camera, an altimeter, a barometer, an optical blood flow sensor, an electrocardiogram sensor, an inertial sensor, a geo-positioning system, an optical sensor, a thermometer, an electro-myography sensor, and the like.

The NPU 100 may obtain cardiovascular disease prediction artificial neural network model (fusion artificial neural network (ANN)) data locality information from the compiler 200.

The NPU 100 may output N results (e.g., heterogeneous inference results) through N output units. The heterogeneous data output from the NPU 100 may be classification, semantic segmentation, object detection, prediction, or the like.

Referring to FIG. 21, the SFU 160 may include a plurality of function units. Each function unit can be selectively operated. Each function unit can be selectively turned on or off. That is, each function unit is configurable.

In other words, the SFU 160 may include various function units required for cardiovascular disease prediction artificial neural network inference operations.

For example, the function unit of the SFU 160 may include a function unit for a skip-connection operation, a function unit for an activation function operation, a function unit for a pooling operation, a function unit for a quantization operation, a function unit for non-maximum suppression (NMS) operation, a function unit for integer to floating-point conversion (INT to FP32), a function unit for batch-normalization operation, a function unit for interpolation operation, a function unit for concatenation operation, a function units for bias operation, and the like.

The function units of the SFU 160 may be selectively turned-on or turned-off by cardiovascular disease prediction artificial neural network data locality information. The artificial neural network data locality information may include turn-off or turn-off-related control information of a corresponding function unit when an operation for a specific layer is performed.

Figure 22A:
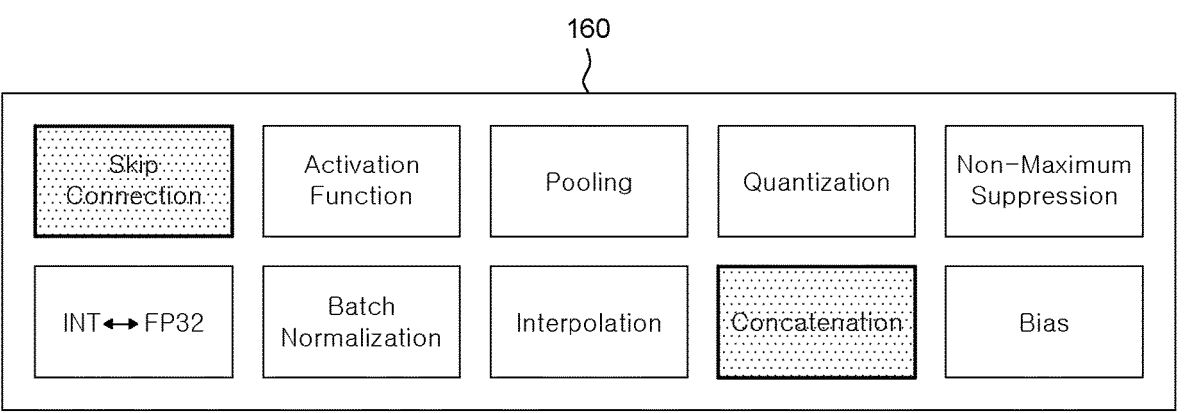
FIG. 22A is an exemplary diagram illustrating an example of the SFU shown in FIG. 20.
Figure 22B:
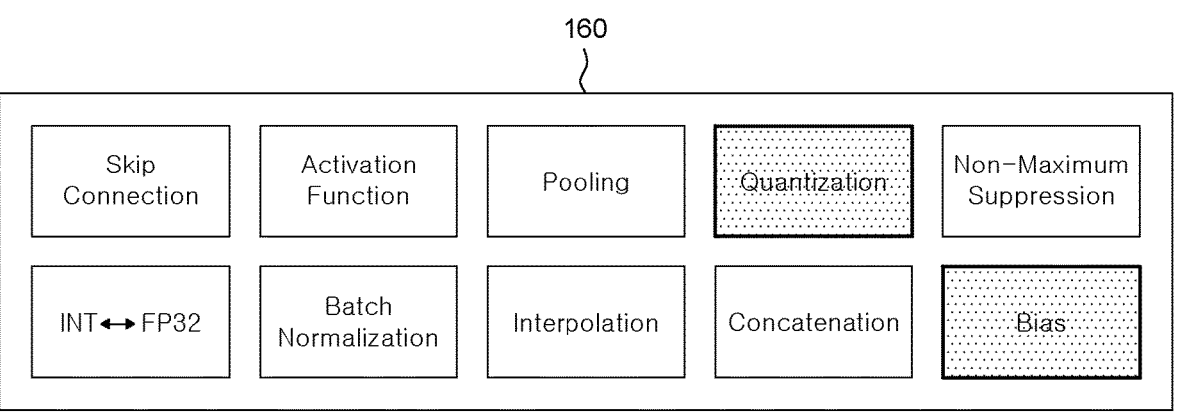
FIG. 22B is an exemplary diagram illustrating another example of the SFU shown in FIG. 20.

FIG. 22A illustrates an example of the SFU shown in FIG. 20, and FIG. 22B illustrates another example of the SFU shown in FIG. 20.

Referring to FIGS. 22A and 22B, activated units among function units of the SFU 160 may be turned on.

Specifically, as shown in FIG. 22A, the SFU 160 may selectively activate a skip-connection operation and a concatenation operation. Illustratively, each activated function unit is marked with hatching in the drawings.

For example, the SFU 160 may concatenate heterogeneous sensor data for a fusion operation. For example, in order to skip-connect the SFU 160, the controller may control the on-chip memory 120 and the SFU 160.

Specifically, as shown in FIG. 22B, the quantization operation and the bias operation can be selectively activated. For example, in order to reduce the size of the feature map data output from the processing element array 110, the quantization function unit of the SFU 160 may receive the output feature map from the processing element array 110 and quantizes the output feature map to a specific bit width. In addition, the quantized feature map may be stored in the on-chip memory 120. A series of operations may be sequentially performed by the controller, and the NPU scheduler 130 may be configured to control the sequence of the operations.

In this way, when selectively turning-off some function units of the SFU 160, it is possible to reduce the power consumption of the NPU 100. Meanwhile, in order to turn-off some function units, power-gating may be applied. Alternatively, clock-gating may be applied to turn-off some function units.

Figure 23:
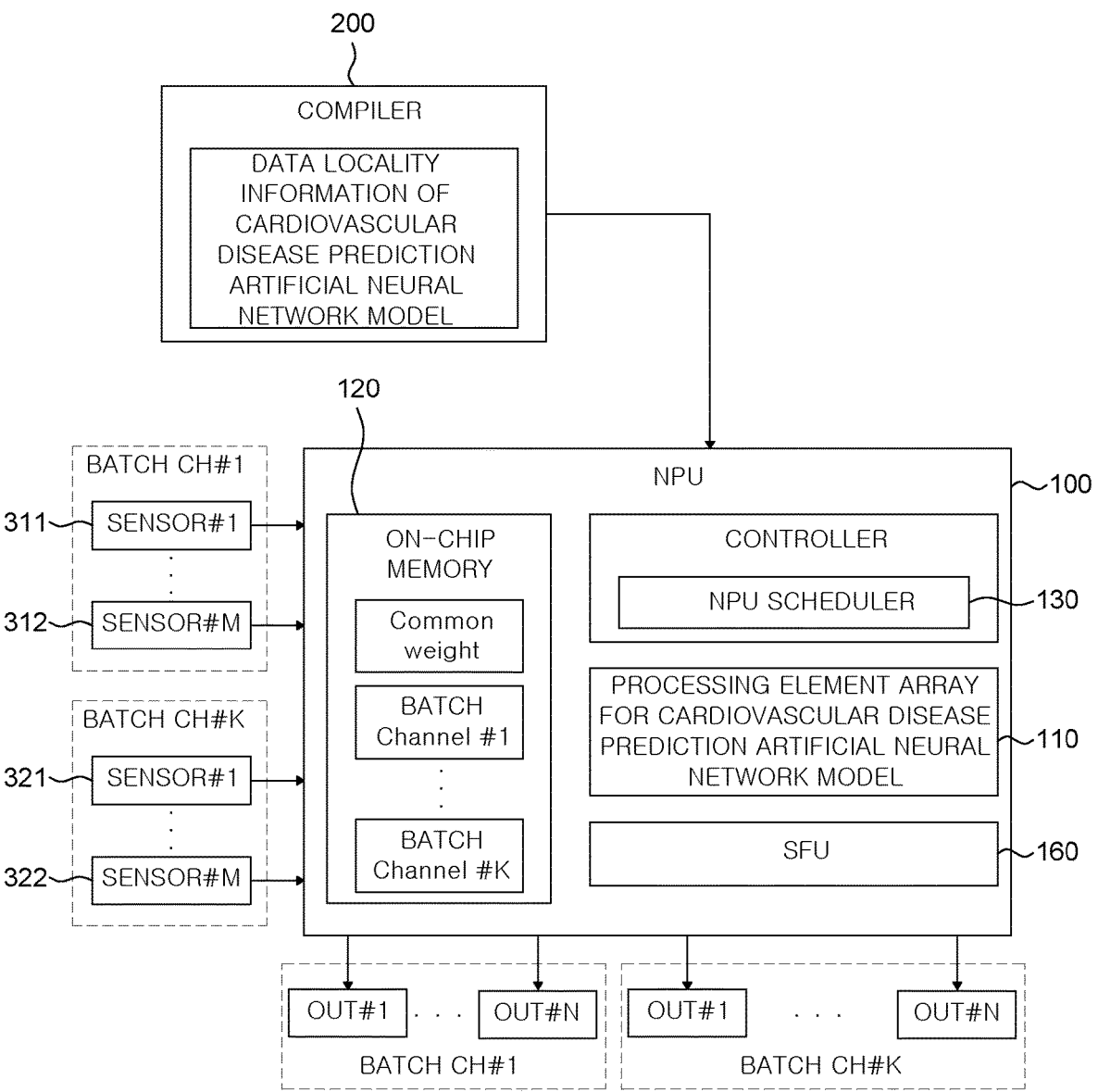
FIG. 23 is a conceptual diagram illustrating a system including an NPU architecture according to a sixth example of the present disclosure.

FIG. 23 illustrates a system including an NPU architecture according to a sixth example.

Referring to FIG. 23, a NPU batch-mode may be applied. The NPU 100 to which batch mode is applied may include a processing element array 110 for a cardiovascular disease prediction artificial neural network model, an on-chip memory 120, an NPU scheduler 130, and a special function unit (SFU) 160.

The NPU scheduler 130 may be included in the controller as illustrated.

The NPU 100 may obtain artificial neural network data locality information of an artificial neural network model for predicting cardiovascular disease from the compiler 200.

The batch-mode disclosed in this example may be referred to as a mode configured to achieve low-power consumption by sequentially processing a plurality of identical sensors with one cardiovascular disease prediction artificial neural network model to reuse the weights of the one cardiovascular disease prediction artificial neural network model as much as the number of the plurality of identical sensors.

For batch-mode operation, the controller of the NPU 100 may be configured to control the NPU scheduler 130 so that the weight stored in the on-chip memory is reused as much as the number of sensors input to each batch-channel. That is, the NPU 100 may be configured to operate in a batch-mode with M sensors. In this case, the batch-mode operation of the NPU 100 may be configured to operate with a cardiovascular disease prediction artificial neural network model.

For the operation of the cardiovascular disease prediction artificial neural network, the NPU 100 may be configured to have a plurality of batch-channels #1 to #K for fusion. Each batch-channel may be configured to include the same number of the plurality of sensors. The first batch-channel #1 may include a plurality of first sensors. In this case, the number of first sensors may be M. The Kth batch-channel #K may include a plurality of second sensors. In this case, the number of second sensors may be M.

The NPU 100 may reuse and process a weight corresponding to the input from the sensors 311 and 312 in the on-chip memory 120 through the first batch-channel. In addition, the NPU 100 may reuse and process the weight corresponding to the input from the sensors 321 and 322 in the on-chip memory 120 through the second batch-channel.

In this way, the NPU 100 may receive inputs from various sensors through a plurality of batch-channels, reuse weights, and process the cardiovascular disease prediction artificial neural network in a batch-mode. A sensor of at least one channel among the plurality of batch-channels and a sensor of at least one other channel may be different from each other.

The on-chip memory 120 in the NPU 100 may be configured to have a storage space corresponding to a plurality of batch-channels.

The NPU scheduler 130 in the NPU 100 may operate the processing element array 110 according to the batch-mode.

The SFU 160 in the NPU 100 may provide a special function for processing at least one fusion operation.

The NPU 100 may deliver each output through a plurality of batch-channels.

At least one of the plurality of batch channels may be inferred data of a cardiovascular disease prediction artificial neural network model.

Figure 24:
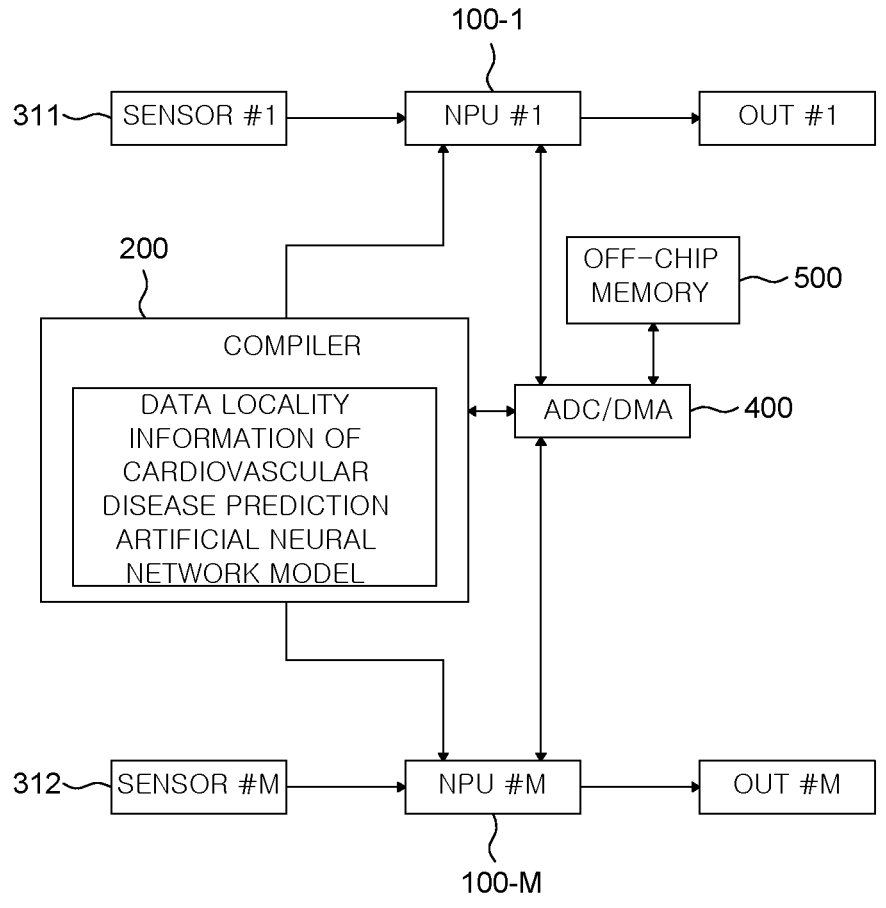
FIG. 24 is an exemplary diagram illustrating an example of utilizing a plurality of NPUs according to a seventh example of the present disclosure.
Figure 25:
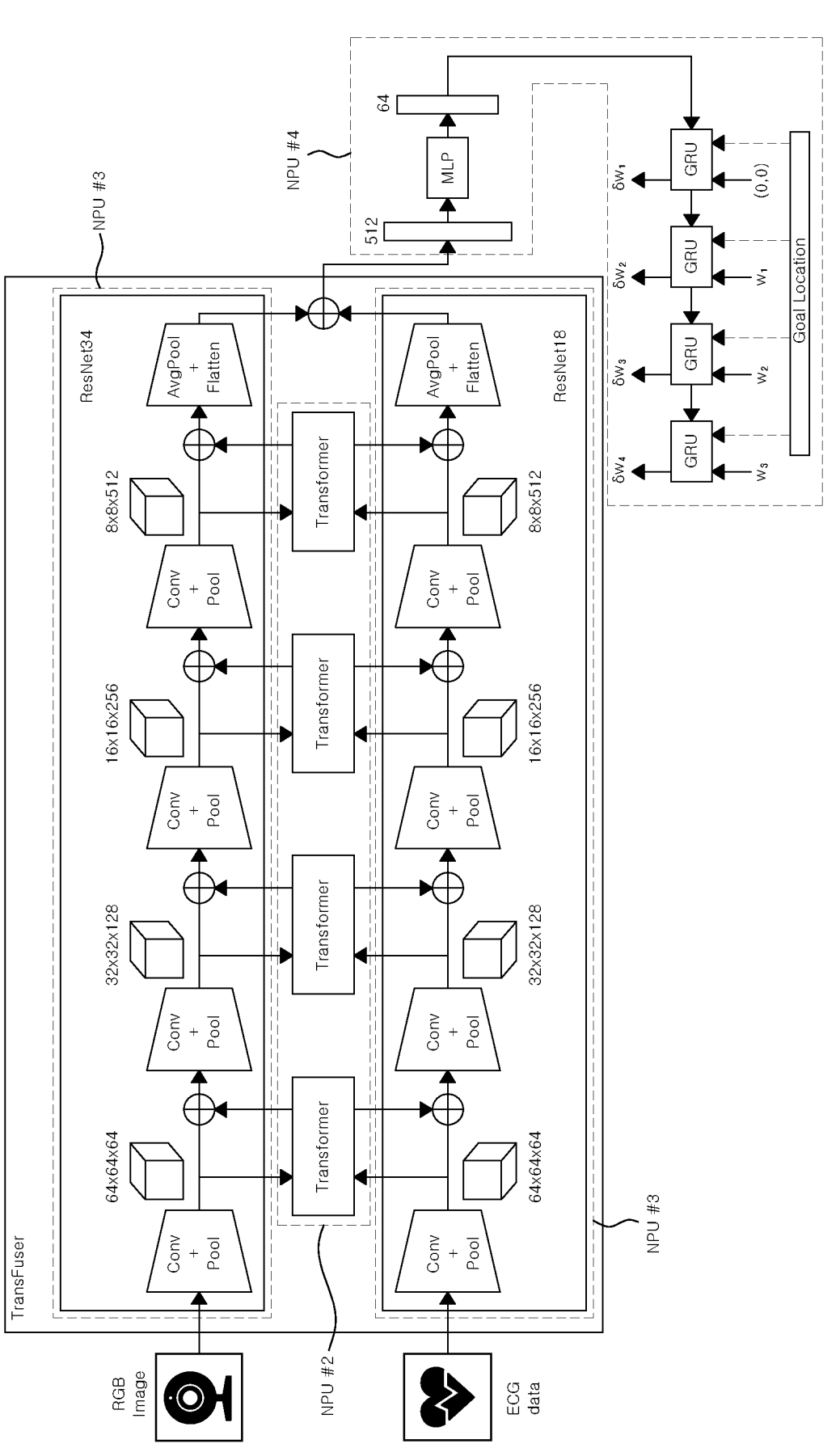
FIG. 25 is an exemplary diagram illustrating an example of processing the fusion artificial neural network shown in FIG. 12 through a plurality of NPUs shown in FIG. 24.

FIG. 24 illustrates an example of utilizing a plurality of NPUs according to the seventh example. FIG. 25 illustrates an example of processing the fusion artificial neural network shown in FIG. 12 through a plurality of NPUs shown in FIG. 24.

Referring to FIG. 24, a plurality of, illustratively, M NPUs may be used to predict cardiovascular disease. Among the M NPUs, the first NPU 100-1 may process data provided from, for example, the sensor #1 311, and the Mth NPU 100-M may, for example, process data provided from the sensor #M 312 can be processed. The plurality of NPUs (e.g., 100-1 and 100-2) may access the off-chip memory 500 through ADC/direct memory access (DMA) 400.

The plurality of NPUs (e.g., 100-1 and 100-2) may obtain artificial neural network data locality information of an artificial neural network model for predicting cardiovascular disease from the compiler 200.

Each NPU may process a cardiovascular disease prediction artificial neural network and transfer an operation for fusion to different NPUs through the ADC/DMA 400.

The ADC/DMA 400 may obtain data locality information for an artificial neural network of a fusion cardiovascular disease prediction artificial neural network model from the compiler 200.

The compiler 200 may generate the artificial neural network data locality information of the artificial neural network model by dividing it into data locality information #1 and data locality information #M so that operations that need to be processed in parallel among operations that can be processed in each NPU according to artificial neural network data locality information of the cardiovascular disease prediction artificial neural network model.

The off-chip memory 500 may store data that can be shared by a plurality of NPUs, and may be transmitted to each NPU.

As shown in FIG. 25, NPU #1 may be in charge of the first artificial neural network for processing data provided from the camera, and NPU #2 may be in charge of the second artificial neural network for processing data provided from ECG sensor. In addition, the NPU #2 may be in charge of conversion for the fusion of the first artificial neural network and the second artificial neural network.

An NPU for an artificial neural network model for predicting cardiovascular disease according to various examples of the present disclosure has been described. According to the present disclosure, it is possible to accurately predict the onset probability and diagnosis result of cardiovascular disease through a device carried by a user. In particular, the present disclosure can accurately predict the onset probability and diagnosis result of cardiovascular disease on its own without sharing personal sensing data in the cloud or transmitting it to a server for diagnosis.

The examples illustrated in the specification and the drawings are merely provided to facilitate the description of the subject matter of the present disclosure and to provide specific examples to aid the understanding of the present disclosure and it is not intended to limit the scope of the present disclosure. It is apparent to those of ordinary skill in the art to which the present disclosure pertains in which other modifications based on the technical spirit of the present disclosure can be implemented in addition to the examples disclosed herein.

[National R&D Project Supporting This Invention]
[Project Identification Number] 1711160627
[Task Number] 2022-0-00159-001
[Name of Ministry] Ministry of Science and ICT
[Name of Task Management (Specialized) Institution] Institute of Information & Communications Technology Planning & Evaluation
[Research Project Title] Smart Edge Device Technology Development (R&D)
[Research Task Name] Digital markers and intelligent edge device development for the prediction of senior cardiovascular and cerebrovascular diseases and dementia.
[Contribution rate] 1/1
[Name of the organization performing the task] Korea Advanced Institute of Science and Technology (KAIST)
[Research Period] 2022.04.01-2022.12.31

What is claimed is:

1. A neural processing unit (NPU) implemented in hardware, the NPU comprising:

a controller configured to receive a compiled machine code of an artificial neural network (ANN) model for predicting cardiovascular disease, the ANN model configured to receive sensing data of at least one of ECG, respiration, pulse rate, acceleration, and body temperature and to output a probability of disease onset for at least one disease among cerebral infarction, heart failure, and ischemic heart disease;

an input circuit configured to receive a plurality of input signals from M heterogeneous sensors corresponding to the ANN model;

a processing element (PE) array formed as an N×M matrix and configured to perform a calculation of the ANN model, the ANN model including computation of at least one fusion layer that combines multiple sensing data to output fused data of the M heterogeneous sensors;

a special function unit (SFU) configured to perform a special function of calculating the ANN model; and an on-chip memory configured to store operation data of the ANN model, wherein the controller is further configured to control the execution of the PE array, the SFU, and the on-chip memory in a sequence optimized based on data locality information of the ANN model included in the compiled machine code, and selectively delete non-reusable data during the computation of the at least one fusion layer based on the on-chip memory data locality information of the ANN model, and

wherein the controller is further configured such that a size of data of one of the M heterogeneous sensors is scaled up or scaled down so that data sizes of one axis of the fused data of the M heterogeneous sensors are equal, and the PE array has a utilization rate that varies according to a size of at least one axis of heterogeneous sensor data.

2. The NPU of claim 1, wherein the ANN model is further configured to output the probability of disease onset for the at least one disease by inputting the sensing data of at least two of the ECG, the respiration, the pulse rate, the acceleration, and the body temperature.

3. The NPU of claim 1, wherein the ANN model is further configured to input the sensing data of at least two of the ECG, the respiration, the pulse rate, the acceleration, and the body temperature and to output a probability of disease onset for at least two diseases among cerebral infarction, heart failure, and ischemic heart disease.

4. The NPU of claim 1, further comprising:

an output unit configured to output a diagnosis result of the at least one disease of the ANN model, wherein the ANN model is trained to process an inference operation of at least one of classification, semantic segmentation, object detection, and prediction by the PE array.

5. The NPU of claim 1, wherein the SFU has at least one function of a skip-connection and a concatenation for fusion of artificial neural networks.

6. The NPU of claim 1, wherein the controller includes a scheduler, and wherein the scheduler is configured to control the on-chip memory to preserve specific data stored in the on-chip memory up to a specific operation stage of the ANN model based on the data locality information of the ANN model.

7. The NPU of claim 1, wherein the PE array includes a plurality of threads, and wherein the controller is further configured to control the plurality of threads to process a parallel section of the ANN model based on the data locality information of the ANN model.

8. A neural processing unit (NPU) implemented in hardware, the NPU comprising:

a controller configured to receive a machine code of an artificial neural network (ANN) model for predicting cardiovascular disease, the ANN configured to input sensing data of at least one of ECG, respiration, pulse rate, acceleration, and body temperature and to output a probability of disease onset for at least one disease among cerebral infarction, heart failure, and ischemic heart disease, the sensing data being input from M heterogeneous sensors;

a processing element (PE) array formed as an N×M matrix and configured to perform computation of the ANN model based on the machine code, the ANN model including computation of at least one fusion layer that combines multiple sensing data to output fused data of the M heterogeneous sensors; and a special function unit (SFU) configured to compute a corresponding special function by receiving a convolution operation value processed by the PE array, wherein the SFU includes a plurality of function units and is further configured to selectively control at least one of the plurality of function units in a sequence optimized according to data locality information of the ANN model included in the machine code, wherein the controller is further configured to selectively delete non-reusable data during the computation of the at least one fusion layer based on the memory data locality information of the ANN model, and wherein the controller is further configured such that a size of data of one of the M heterogeneous sensors is scaled up or scaled down so that data sizes of one axis of the fused data of the M heterogeneous sensors are equal, and the PE array has a utilization rate that varies according to a size of at least one axis of heterogeneous sensor data.

9. The NPU of claim 8, wherein the plurality of function units are configured in a pipeline structure.

10. The NPU of claim 8, wherein the plurality of function units are configured to be selectively activated by the controller.

11. The NPU of claim 8, wherein the plurality of function units are configured to be selectively deactivated by the controller.

12. The NPU of claim 8, wherein each of the plurality of function units is configured to be selectively clock-gated for each specific operation stage by the controller.

13. The NPU of claim 8, wherein each of the plurality of function units is configured to be selectively power-gated for each specific operation stage by the controller.

14. The NPU of claim 8, further comprising:

an input unit configured to receive a plurality of input signals corresponding to the ANN model; and an on-chip memory configured to store computation data of the ANN model.

15. The NPU of claim 8, further comprising:

a batch input unit configured to receive a plurality of input signals corresponding to the ANN model in a batch-mode;

an on-chip memory configured to store computation data of the ANN model in the batch-mode; and an output unit configured to output at least one inference result of the ANN model, wherein the ANN model is trained to process an inference operation of at least one of classification, semantic segmentation, object detection, and prediction by the PE array in the batch-mode.

16. A system comprising:

at least one neural processing unit (NPU) implemented in hardware, the NPU including a controller configured to receive a machine code of an artificial neural network (ANN) model for predicting cardiovascular disease, the ANN model configured to input sensing data of at least one of ECG, respiration, pulse rate, acceleration, and body temperature and to output a probability of disease onset for at least one disease among cerebral infarction, heart failure, and ischemic heart disease, an input unit configured to receive a plurality of input signals from M heterogeneous sensors corresponding to the ANN model, a processing element array formed as an N×M matrix and configured to perform a convolution operation including computation of at least one fusion layer that combines multiple sensing data to output fused data of the M heterogeneous sensors, and an on-chip memory configured to store a result of the convolution operation; and a memory controller including a memory, the memory controller configured to receive data locality information of the ANN model, the data locality information of the ANN model predicting successive memory operation requests in an optimized sequence of the at least one neural processing unit, and cache a next memory operation request to be requested by a corresponding one of the at least one neural processing unit based on the data locality information, wherein the controller is further configured to selectively delete non-reusable data during the computation of the at least one fusion layer based on the on-chip memory data locality information of the ANN model, and wherein the controller is further configured such that a size of data of one of the M heterogeneous sensors is scaled up or scaled down so that data sizes of one axis of the fused data of the M heterogeneous sensors are equal, and the PE array has a utilization rate that varies according to a size of at least one axis of heterogeneous sensor data.

17. The system of claim 16, wherein the at least one neural processing unit is plural, and wherein the machine code of the ANN model input to the controller of each neural processing unit is configured to be processed in parallel in the plurality of neural processing units.

18. The system of claim 16, wherein the at least one neural processing unit is plural, and wherein the machine code is compiled for parallel processing in the plurality of neural processing units.

19. The system of claim 16, wherein the at least one neural processing unit is plural, and wherein the memory controller is configured to directly control a parallel processing of the plurality of neural processing units.

* * * * *